United States Patent
Yi-Lin et al.

(10) Patent No.: US 7,199,265 B2
(45) Date of Patent: Apr. 3, 2007

(54) THYROID RECEPTOR LIGANDS, PHARMACEUTICAL COMPOSITIONS COMPRISING THEM AND THEIR USE IN THE TREATMENT OF DISORDERS INFLUENCED BY THYROID HORMONES

(75) Inventors: Li Yi-Lin, Huddinge (SE); Johan Malm, Skogås (SE); Chris Litten, Tumba (SE); Ana Maria Garcia Collazo, Stockholm (SE); Neeraj Garg, Tumba (SE)

(73) Assignee: Karo Bio AB, Huddinge (SE)

( * ) Notice: Subject to any disclaimer, the term of this patent is extended or adjusted under 35 U.S.C. 154(b) by 258 days.

(21) Appl. No.: 10/311,524
(22) PCT Filed: Jun. 15, 2001
(86) PCT No.: PCT/EP01/06815

§ 371 (c)(1),
(2), (4) Date: Apr. 22, 2003

(87) PCT Pub. No.: WO01/98256

PCT Pub. Date: Dec. 27, 2001

(65) Prior Publication Data

US 2004/0097589 A1    May 20, 2004

(30) Foreign Application Priority Data

Jun. 21, 2000    (GB) ................... 0015205.8

(51) Int. Cl.
*C07C 321/00*    (2006.01)
*C07C 315/00*    (2006.01)
*C07C 229/00*    (2006.01)
*C07D 215/00*    (2006.01)
*C07D 209/00*    (2006.01)

(52) U.S. Cl. ............... 562/426; 562/427; 562/430; 562/439; 562/448; 562/455; 560/9; 560/10; 560/12; 560/34; 560/45; 564/92; 546/146; 546/168; 546/234; 546/300; 548/486; 548/491

(58) Field of Classification Search ......... 562/426, 562/427, 430, 439, 448, 455; 560/45, 12, 560/9, 10, 34; 564/92; 546/168, 146, 234, 546/300; 548/486, 491
See application file for complete search history.

(56) References Cited

U.S. PATENT DOCUMENTS

| | | | | |
|---|---|---|---|---|
| 3,652,665 A | * | 3/1972 | Shen ................ | 562/474 |
| 4,738,711 A | * | 4/1988 | Barton et al. ........ | 504/182 |
| 5,569,674 A | * | 10/1996 | Yokoyama et al. ..... | 514/539 |
| 5,883,133 A | * | 3/1999 | Schwark et al. ...... | 514/619 |
| 5,883,294 A | | 3/1999 | Scanlan et al. | |
| 6,545,018 B2 | * | 4/2003 | Chiang et al. ....... | 514/307 |

FOREIGN PATENT DOCUMENTS

| | | | |
|---|---|---|---|
| EP | 0 580 550 A | | 1/1994 |
| GB | 642159 | * | 8/1950 |
| GB | 643089 | * | 9/1950 |
| WO | WO 96/05190 A | | 2/1996 |

OTHER PUBLICATIONS

SChmid, CA 132:21239, abstract of GIT Fachzeitscrift fuer das Laboratorium, vol. 40(11), pp. 1129-1131, 1996.*

* cited by examiner

*Primary Examiner*—Sikarl A. Witherspoon
(74) *Attorney, Agent, or Firm*—Todd E. Garabedian; Wiggin and Dana LLP

(57) ABSTRACT

This invention relates to compounds of the formula (I) which are thyroid receptor ligands, and are preferably selective for the thyroid hormone receptor β, to methods of preparing such compounds and to methods for using such compounds such as in the regulation of metabolism.

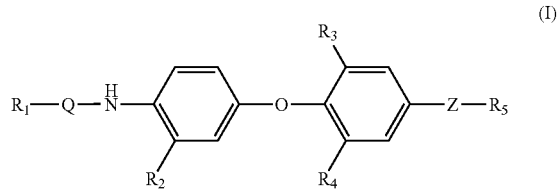

3 Claims, No Drawings

THYROID RECEPTOR LIGANDS, PHARMACEUTICAL COMPOSITIONS COMPRISING THEM AND THEIR USE IN THE TREATMENT OF DISORDERS INFLUENCED BY THYROID HORMONES

CROSS-REFERENCE TO RELATED APPLICATIONS

This is an application filed under 35 USC §371 of International Application No. PCT/EP01/06815 filed 15 Jun. 2001.

FIELD OF THE INVENTION

This invention relates to novel compounds which are thyroid receptor ligands, and are preferably selective for the thyroid hormone receptor β, to methods of preparing such compounds and to methods for using such compounds such as in the regulation of metabolism.

BACKGROUND OF THE INVENTION

While the extensive role of thyroid hormones in regulating metabolism in humans is well recognized, the discovery and development of new specific drugs for improving the treatment of hyperthyroidism and hypothyroidism has been slow. This has also limited the development of thyroid hormone agonists and antagonists for treatment of other important clinical indications, such as hypercholesterolemia, obesity and cardiac arrhythmias.

Thyroid hormones affect the metabolism of virtually every cell of the body. At normal levels, these hormones maintain body weight, the metabolic rate, body temperature, and mood, and influence serum low density lipoprotein (LDL) levels. Thus, in hypothyroidism there is weight gain, high levels of LDL cholesterol, and depression. In excess with hyperthyroidism, these hormones lead to weight loss, hypermetabolism, lowering of serum LDL levels, cardiac arrhythmias, heart failure, muscle weakness, bone loss in postmenopausal women, and anxiety.

Thyroid hormones are currently used primarily as replacement therapy for patients with hypothyroidism. Therapy with L-thyroxine returns metabolic functions to normal and can easily be monitored with routine serum measurements of levels of thyroid-stimulating hormone (TSH), thyroxine (3,5,3',5'-tetraiodo-L-thyronine, or $T_4$) and triiodothyronine (3,5,3'-triiodo-L-thyronine, or $T_3$). However, replacement therapy, particularly in older individuals is limited by certain of the deleterious effects of thyroid hormones.

In addition, some effects of thyroid hormones may be therapeutically useful in non-thyroid disorders if adverse effects can be minimized or eliminated. These potentially useful influences include weight reduction, lowering of serum LDL levels, amelioration of depression and stimulation of bone formation. Prior attempts to utilize thyroid hormones pharmacologically to treat these disorders have been limited by manifestations of hyperthyroidism and in particular by cardiovascular toxicity.

Development of specific and selective thyroid hormone receptor agonists could lead to specific therapies for these common disorders while avoiding the cardiovascular and other toxicities of native thyroid hormones. Tissue-selective thyroid hormone agonists may be obtained by selective tissue uptake or extrusion, topical or local delivery, targeting to cells through other ligands attached to the agonist and targeting receptor subtypes. Thyroid hormone receptor agonists that interact selectively with the β-form of the thyroid hormone receptor offers an especially attractive method for avoiding cardio-toxicity.

Thyroid hormone receptors (TRs) are, like other nuclear receptors, single polypeptide chains. The various receptor forms appear to be products of two different genes, α and β. Further isoform differences are due to the fact that differential RNA processing results in at least two isoforms from each gene. The $TR\alpha_1$, $TR\beta_1$ and $TR\beta_2$ isoforms bind thyroid hormone and act as ligand-regulated transcription factors. In adults, the $TR\beta_1$ isoform is the most prevalent form in most tissues, especially in the liver and muscle. The $TR\alpha_2$ isoform is prevalent in the pituitary and other parts of the central nervous system, does not bind thyroid hormones, and acts in many contexts as a transcriptional repressor. The $TR\alpha_1$ isoform is also widely distributed, although its levels are generally lower than those of the $TR\beta_1$ isoform. This isoform may be especially important for development. Whereas many mutations in the TRβ gene have been found and lead to the syndrome of generalized resistance to thyroid hormone, mutations leading to impaired TRα function have not been found.

A growing body of data suggest that many or most effects of thyroid hormones on the heart, and in particular on the heart rate and rhythm, are mediated through the α-form of the $TR\alpha_1$ isoform, whereas most actions of the hormone such as on the liver, muscle and other tissues are mediated more through the β-forms of the receptor. Thus, a TRβ-selective agonist might not influence the cardiac rhythm and rate, but would elicit many other actions of the hormones. It is believed that the α-form of the receptor is the major drive of heart rate for the following reasons: (i) tachycardia is very common in the syndrome of generalized resistance to thyroid hormone in which there are defective TRβ-forms, and high circulating levels of $T_4$ and $T_3$; (ii) there was a tachycardia in the only described patient with a double deletion of the TRβ gene (Takeda et al, *J. Clin. Endrocrinol. & Metab.* 1992, 74, p 49); (iii) a double knockout TRα gene (but not β-gene) in the mouse has a slower pulse than control mice (Forrest D and Vennstrom B, *Thyroid* 2000, 10(1), 41–52); (iv) western blot analysis of human myocardial TRs show presence of the $TR\alpha_1$, $TR\alpha_2$ and $TR\beta_2$ proteins, but not $TR\beta_1$.

If these indications are correct, then it may be possible that a TRβ-selective agonist could be used to mimic a number of thyroid hormone actions, while having a lesser effect on the heart. Such a compound may be used for: (i) replacement therapy in elderly subjects with hypothyroidism who are at risk for cardiovascular complications; (ii) replacement therapy in elderly subjects with subclinical hypothyroidism who are at risk for cardiovascular complications, (iii) obesity; (iv) hypercholesterolemia due to elevations of plasma LDL levels; (v) depression; (vi) osteoporosis in combination with a bone resorption inhibitor.

DESCRIPTION OF THE INVENTION

In accordance with the present invention, compounds are provided which are thyroid receptor ligands, and have the general formula I:

Structure I

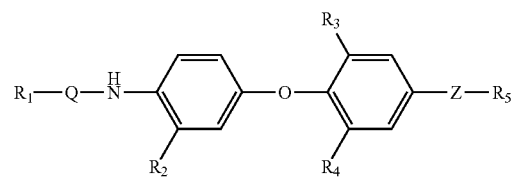

or pharmaceutically acceptable salts thereof, wherein:

$R_1$ is selected from $C_{6-15}$ aryl; $C_{5-15}$ heteroaryl; $C_{1-20}$ alkyl; $C_{2-20}$ alkenyl; $C_{2-20}$ alkynyl; $C_{3-15}$ cycloalkyl, said alkyl, alkenyl, alkynyl, cycloalkyl, being optionally substituted with 1, 2 or 3 groups $R^a$ which groups may be the same or different, said aryl and heteroaryl being optionally substituted with 1, 2 or 3 groups of $R^b$ which groups may be the same or different;

$R_2$ is selected from hydrogen; halogen; —$NO_2$; —CN; $C_{6-10}$ aryl; $C_{5-10}$ heteroaryl; $C_{1-10}$ alkyl; $C_{3-8}$ cycloalkyl; $C_{2-10}$ alkenyl; $C_{2-10}$ alkynyl, said alkyl, cycloalkyl, alkenyl, alkynyl optionally substituted with 1, 2 or 3 groups $R^a$ which groups may be the same or different, said aryl, heteroaryl optionally substituted with 1, 2 or 3 groups of $R^b$ which groups may be the same or different;

$R_1$ can be linked through the available atoms to position $R_2$, thus forming an aza containing $C_5$–$C_8$ heterocyclic ring, saturated or partially unsaturated, and optionally substituted with 1, 2 or 3 groups of $R^c$ which groups may be the same or different;

Q is selected from —CO—; —SO—; —$SO_2$—; —NHCS— or —NHCO—;

$R_3$ and $R_4$ are independently selected from: halogen; $C_{1-4}$ alkyl; $C_{3-4}$ cycloalkyl; $C_{2-4}$ alkenyl; and $C_{2-4}$ alkynyl, said alkyl, cycloalkyl, alkenyl, alkynyl, or a bioisosteric equivalent thereof and optionally substituted with 1, 2 or 3 groups $R^d$ which groups may be the same or different;

Z is selected from —$(CH_2)_n$—; —CH=CH—; —$O(CH_2)_m$—; and —$NH(CH_2)_m$—;

n is 0, 1, 2 or 3;

m is 1 or 2;

$R_5$ is independently selected from: carboxylic acid (—$CO_2H$); phosphonic acid (—$PO(OH)_2$); phosphamic acid (—$PO(OH)NH_2$); sulphonic acid (—$SO_2OH$); hydroxamic acid (—CONHOH); oxamic acid (—$NHCOCO_2H$); malonamic acid (—$NHCOCH_2CO_2H$); acylsulphonamide (—$CONHSO_2R'$); and a carboxylic acid amide (—CONR'R") where the amine portion of the amide is derived either from a L or D α-amino acid, or from a mixture of L and D α-aminoacid stereoisomers such that the general structure —CONR'R" can be represented by:

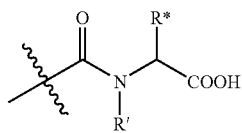

where R* is any of the side chains found in the naturally occuring α-amino acids, including those examples wherein R' and R* are connected to form 4 to 8-membered rings (such as when R' and R* comprise consecutive —$(CH_2)$— groups to form proline or homoproline);

or any other possible bioisosteric equivalent of all the groups above;

$R^a$ is selected from: hydrogen; halogen; —CN; —$CO_2H$; —CHO; —$NO_2$; $C_{6-10}$ aryl; $C_{5-10}$ heteroaryl; $C_{1-4}$ alkoxy; $C_{2-4}$ alkenoxy; $C_{2-4}$ alkynoxy; $C_{6-10}$ aryloxy; $C_{5-10}$ heteroaryloxy; $C_{1-4}$ alkylthio; $C_{2-4}$ alkenylthio; $C_{2-4}$ alkynylthio; $C_{6-10}$ arylthio; $C_{5-10}$ heteroarylthio; —$N(C_{1-6}$ alkyl$)_2$; —$NH(C_{1-6}$ alkyl); —$N(C_{2-6}$ alkenyl$)_2$; —$NH(C_{2-6}$ alkenyl); —$N(C_{6-10}$ aryl$)_2$; —$NH(C_{6-10}$ aryl); —$N(C_{5-10}$ heteroaryl$)_2$; —$NH(C_{6-10}$ heteroaryl); —$N(C_{1-6}$ alkyl)($C_{2-6}$ alkenyl); —$N(C_{1-6}$ alkyl)($C_{6-10}$ aryl); —$N(C_{1-6}$ alkyl)($C_{6-10}$ heteroaryl); —$N(C_{2-6}$ alkenyl)($C_{6-10}$ aryl); —$N(C_{2-6}$ alkenyl)($C_{5-10}$ heteroaryl); —$N(C_{6-10}$ aryl)($C_{5-10}$ heteroaryl) or a bioisosteric equivalent thereof;

$R^b$ is selected from: hydrogen; halogen; —CN; —$CO_2H$; —CHO; —$NO_2$; —OH; $C_{1-4}$ alkyl; $C_{2-4}$ alkenyl; $C_{2-4}$ alkynyl; $C_{1-4}$ alkoxy; $C_{2-4}$ alkenoxy; $C_{2-4}$ alkynoxy; $C_{6-10}$ aryloxy; $C_{5-10}$ heteroaryloxy; $C_{1-4}$ alkylthio; $C_{2-4}$ alkenylthio; $C_{2-4}$ alkynylthio; $C_{6-10}$ arylthio; $C_{5-10}$ heteroarylthio; —$N(C_{1-6}$ alkyl$)_2$; —$NH(C_{1-6}$ alkyl); —$N(C_{2-6}$ alkenyl$)_2$; —$NH(C_{2-6}$ alkenyl); —$N(C_{6-10}$ aryl$)_2$; —$NH(C_{6-10}$ aryl); —$N(C_{5-10}$ heteroaryl$)_2$; —$NH(C_{6-10}$ heteroaryl); —$N(C_{1-6}$ alkyl)($C_{2-6}$ alkenyl); —$N(C_{1-6}$ alkyl)($C_{6-10}$ aryl); —$N(C_{1-6}$ alkyl)($C_{6-10}$ heteroaryl); —$N(C_{2-6}$ alkenyl)($C_{6-10}$ aryl); —$N(C_{2-6}$ alkenyl)($C_{5-10}$ heteroaryl); —$N(C_{6-10}$ aryl)($C_{5-10}$ heteroaryl) or a bioisosteric equivalent thereof;

$R^c$ is selected from: hydrogen; $C_{1-4}$ alkyl; $C_{2-4}$ alkenyl; $C_{2-4}$ alkynyl or a bioisosteric equivalent;

$R^d$ is selected from: hydrogen; halogen, or a bioisosteric equivalent;

Included for the variables above are all the possible stereoisomers thereof; prodrug ester forms thereof; and pharmaceutically acceptable salts thereof;

In addition, in accordance with the present invention, a method for preventing, inhibiting or treating a disease associated with metabolism dysfunction or which is dependent upon the expression of a $T_3$ regulated gene is provided, wherein a compound of formula I is administered in a therapeutically effective amount. The compound of formula I is preferably an agonist that is preferably selective for the thyroid hormone receptor-beta. Examples of such diseases associated with metabolism dysfunction or are dependent upon the expression of a $T_3$ regulated gene are set out hereinafter and include obesity, hypercholesterolemia, atherosclerosis, cardiac arrhythmias, depression, osteoporosis, hypothyroidism, goiter, thyroid cancer as well as glaucoma and congestive heart failure.

DETAILED DESCRIPTION OF THE INVENTION

The present invention relates to compounds useful as thyroid receptor ligands, and are preferably selective for the thyroid hormone receptor β, and have the general formula I as described above.

One embodiment of the present invention relates to compounds according to the general formula I, wherein $R_1$ is selected from $C_{6-10}$ aryl, $C_{5-9}$ heteroaryl, $C_{1-10}$ alkyl, $C_{2-10}$ alkenyl, $C_{2-10}$ alkynyl or $C_{3-10}$ cycloalkyl; $R_2$ is selected from hydrogen, halogen, $C_{6-10}$ aryl or $C_{1-4}$ alkyl; $R_3$ and $R_4$ is selected from halogen and $C_{1-3}$ alkyl; Z is —$(CH_2)_n$— or —CH=CH—; $R_5$ is —$CO_2H$ or a carboxylic acid amide —COR'R"; and n, $R^a$, $R^b$, $R^c$, $R^d$ and Q variables kept as described in claim 1.

Another embodiment of the present invention relates to compounds according to the general formula I, wherein $R_1$ is selected from $C_{6-10}$ aryl, $C_{5-9}$ heteroaryl, $C_{3-10}$ alkyl, $C_{3-10}$ alkenyl or $C_{3-10}$ alkynyl or $C_{3-10}$ cycloalkyl; $R_2$ is selected from hydrogen, halogen or $C_{1-2}$ alkyl; $R_3$ and $R_4$ is selected from chlorine; Z is —$(CH_2)_n$— or —CH=CH—; $R_5$ is —$CO_2H$; $R^a$ is hydrogen, halogen, —$CO_2H$, $C_6$ aryl, —$N(C_{1-4}$ alkyl$)_2$; $R^b$ is hydrogen, halogen, —$CO_2H$, $C_{1-4}$ alkoxy, —$N(C_{1-4}$ alkyl$)_2$; n is 1 or 2;

and the Q variable kept as described in claim 1.

Yet another embodiment of the present invention comprises compounds according to the general formula I, wherein $R_1$ is selected from $C_{3-8}$ alkyl; $R_2$ is selected from hydrogen, halogen or $C_1$ alkyl; $R_3$ and $R_4$ is selected from chlorine; Z is —$(CH_2)_n$— or —CH=CH—; $R_5$ is —$CO_2H$; $R^a$ is hydrogen or fluorine; n is 1 or 2; Q is —CO—.

Compounds of the invention include, but are not limited to, the following:

3,5-Dichloro-4-(3-bromo-4-isobutyramidophenoxy)phenylacetic acid;
3,5-Dichloro-4-(4-isobutyramidophenoxy)phenylacetic acid;
3,5-Dichloro-4-(3-phenyl-4-isobutyramidophenoxy)phenylacetic acid;
3,5-Dichloro-4-(3-bromo-4-[3-methylcrotonylamido]phenoxy)phenylacetic acid;
3,5-Dichloro-4-(3-isopropylidene-1,3-dihydro-2-oxy-5-indoloxy)phenylacetic acid;
3,5-Dichloro-4-(3-isopropyl-1,3-dihydro-2-oxy-5-indoloxy)phenylacetic acid;
3,5-Dichloro-4-(3-bromo-4-acetamidophenoxy)phenylacetic acid;
3,5-Dichloro-4-(4-acetamido-3-phenylphenoxy)phenylacetic acid;
N-[3,5-dichloro-4-(4-isobutyramidophenoxy)phenylacetyl]glycine;
L-N-[3,5-dichloro-4-(4-isobutyramidophenoxy)phenylacetyl]alanine;
L-N-[3,5-dichloro-4-(4-isobutyramidophenoxy)phenylacetyl]valine;
N-[3,5-dichloro-4-(4-isobutyramido-3-bromophenoxy)phenylacetyl]glycine;
L-Methyl-N-[3,5-dichloro-4-(4-isobutyramido-3-bromophenoxy)phenylacetyl]-alanine;
L-N-[3,5-Dichloro-4-(4-isobutyramido-3-bromophenoxy)phenylacetyl]valine;
3,5-Dichloro-4-(4-isobutyramido-3-methylphenoxy)phenylacetic acid;
3,5-Dichloro-4-(4-trifluoroacetamido-3-bromophenoxy)phenylacetic acid;
3,5-Dichloro-4-(4-[2-chloropropionamido]-3-bromophenoxy)phenylacetic acid;
3,5-Dichloro-4-(4-p-fluorobenzamido-3-bromophenoxy)phenylacetic acid;
3,5-Dichloro-4-(4-isobutyramido-3-trifluoromethylphenoxy)phenylacetic acid;
3,5-Dichloro-4-(3-chloro-4-isobutyramidophenoxy)phenylacetic acid;
3,5-Dichloro-4-(1,3-dihydro-2-oxy-5-imidazoloxy)phenylacetic acid;
3,5-Dichloro-4-(3-bromo-4-isobutyramidophenoxy)phenylcinnamic acid;
3,5-Dichloro-4-(3-bromo-4-[2-chloropropionamido]phenoxy)phenylcinnamic acid;
3,5-Dichloro-4-(3-bromo-4-isobutyramidophenoxy)phenylpropionic acid;
3,5-Dichloro-4-(3-bromo-4-p-fluorobenzamidophenoxy)phenylpropionic acid;
3,5-Dichloro-4-(3-bromo-4-[2-chloropropionamido]phenoxy)phenylpropionic acid;
3,5-Dichloro-4-(4-isobutyramidophenoxy)phenylpropionic acid;
3,5-Dichloro-4-(4-[2-chloropropionamido]phenoxy)phenylcinnamic acid;
3,5-Dibromo-4-(3-methyl-1,3-dihydro-2-oxy-5-indoloxy)phenylcinnamic acid;
3,5-Dibromo-4-(3-methyl-1,3-dihydro-2-oxy-5-indoloxy)phenoxyacetic acid;
3,5-Diisopropyl-4-(7-2H-1,4-benzoxazinoxy-3(4H)-one)phenylpropionic acid;
3,5-Dichloro-4-[3-((E)-2-carboxyvinyl)-4-isobutyramidophenoxy]phenylacetic acid;
3,5-Dichloro-4-(3-bromo-4-isobutyramidophenoxy)benzoyl phenylsulfonamide;

and the compounds showed in the table below,

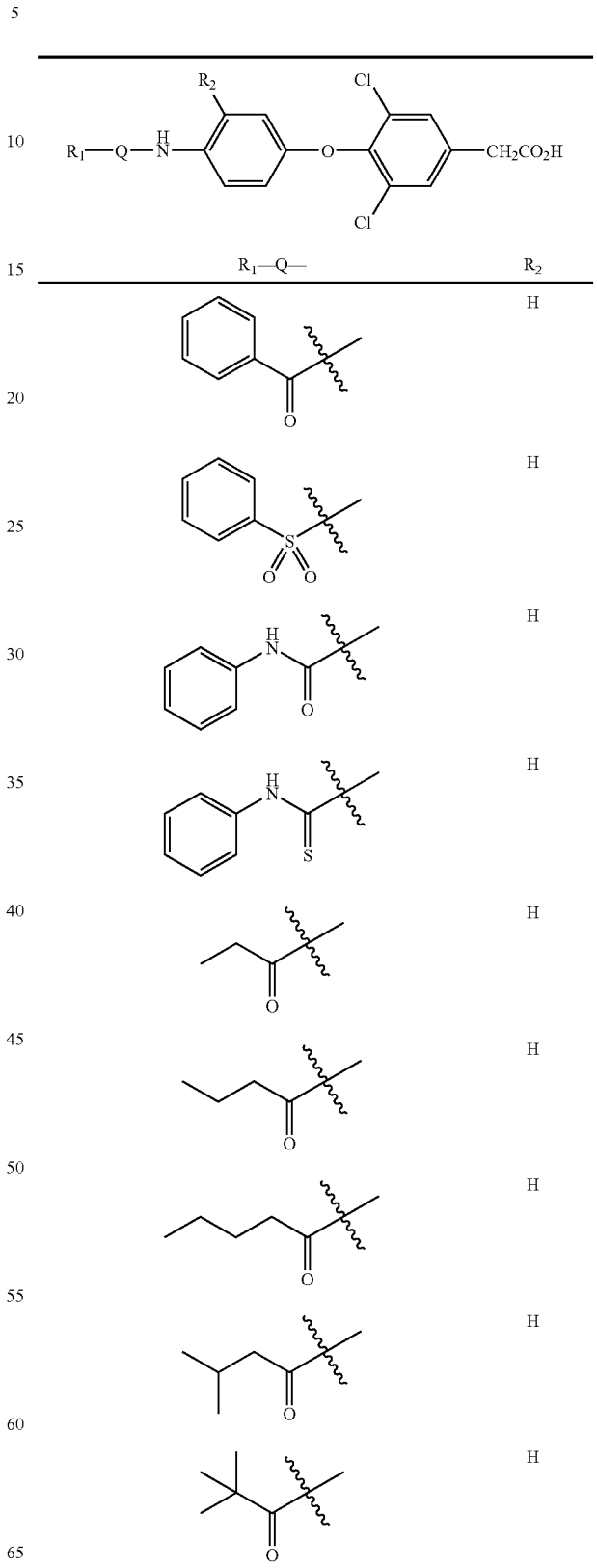

-continued
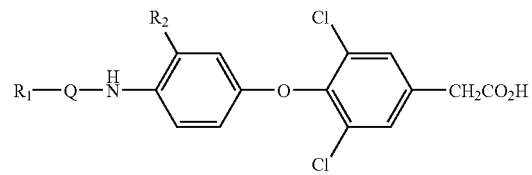
| R₁—Q— | R₂ |
|---|---|
| 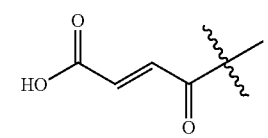 | H |
| 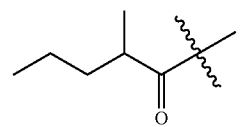 | H |
| 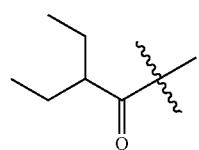 | H |
| 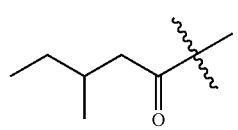 | H |
| 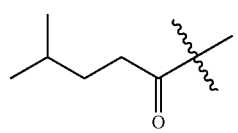 | H |
| 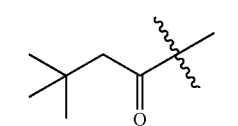 | H |
| 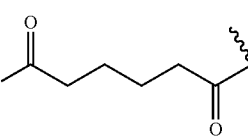 | H |
| 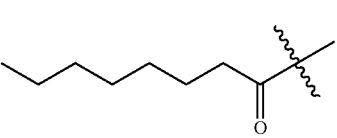 | H |
| 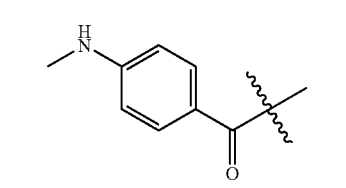 | H |
-continued
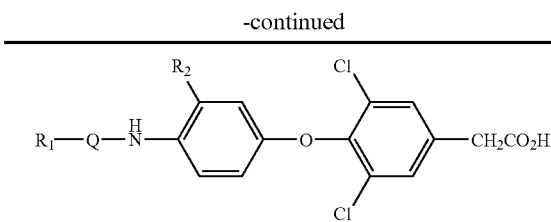
| R₁—Q— | R₂ |
|---|---|
| 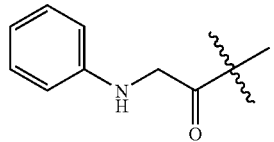 | H |
| 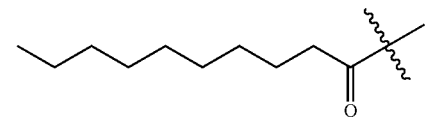 | H |
| 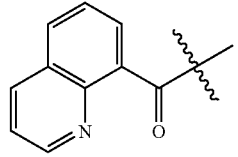 | H |
| 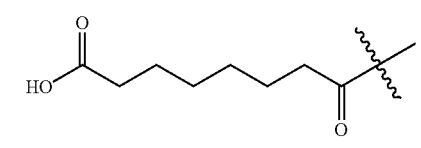 | H |
| 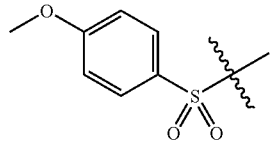 | H |
| 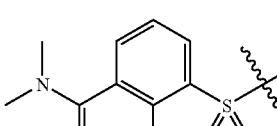 | H |
| 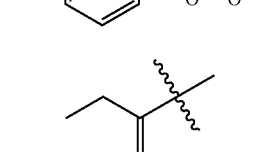 | Br |
| 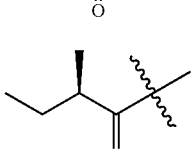 | Br |
| 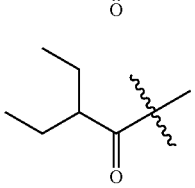 | Br |

-continued

| $R_1$—Q— | $R_2$ |
|---|---|
| (2-ethyl-3-methylbutanoyl group) | Br |
| (4-methylpentanoyl, isobutyl ketone) | Br |
| (1,1-diphenylacetone group) | Br |
| (pyridin-4-ylthio acetone group) | Br |
| (tetrahydroisoquinoline-3-carbonyl group) | H |
| (3-piperidin-1-yl propanoyl group) | B |
| (cyclohexanecarbonyl group) | H |
| (2-propylpentanoyl group) | H |

-continued

| $R_1$—Q— | $R_2$ |
|---|---|
| (2-ethylhexanoyl group) | H |
| (cyclobutanecarbonyl group) | H |
| (cyclopentanecarbonyl group) | H |
| (cycloheptanecarbonyl group) | H |
| (3-methylheptanoyl group) | H |
| (1-methyl-1H-indole-2-carbonyl group) | H |
| (2-(dimethylamino)-3-phenylpropanoyl group) | H |
| (methylsulfonyl group) | H |
| (propylsulfonyl group) | H |

-continued

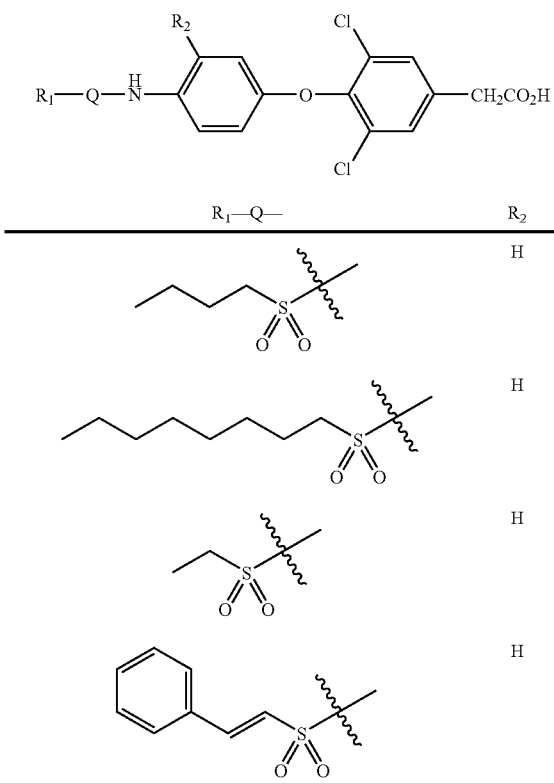

Another embodiment of the present invention is a method for preventing, inhibiting or treating a disease associated with metabolism dysfunction or which is dependent upon the expression of a $T_3$ regulated gene is provided, wherein a compound of formula I is administered in a therapeutically effective amount. The compound of formula I is preferably an agonist that is preferably selective for the thyroid hormone receptor-beta. Examples of such diseases associated with metabolism dysfunction or are dependent upon the expression of a $T_3$ regulated gene are set out hereinafter and include obesity, hypercholesterolemia, atherosclerosis, cardiac arrhythmias, depression, osteoporosis, hypothyroidism, goiter, thyroid cancer as well as glaucoma and congestive heart failure.

Yet another embodiment of the present invention is a method for preventing, inhibiting or treating skin disorders or diseases involving dermal atrophy such as glucocorticoid induced dermal atrophy, inching restoration of dermal atrophy induced by topical glucocorticoids, the prevention of dermal atrophy induced by topical glucocorticoids (such as the simultaneous treatment with topical glucocorticoid or a pharmacological product including both glucocorticoid and a compound of the invention), the restoration/prevention of dermal atrophy induced by systemic treatment with glucocorticoids, restoration/prevention of atrophy in the respiratory system induced by local treatment with glucocorticoids, UV-induced dermal atrophy, or dermal atrophy induced by aging (wrinkles, etc.), wound healing, keloids, stria, cellulite, roughened skin, actinic skin damage, lichen planus, ichtyosis, acne, psoriasis, Dernier's disease, eczema, atopic dermatitis, chloracne, pityriasis and skin scarring.

Exemplifying the invention is a pharmaceutical composition comprising any of the compounds described above and a pharmaceutically acceptable carrier. Also exemplifying the invention is a pharmaceutical composition made by combining any of the compounds described above and a pharmaceutically acceptable carrier. An illustration of the invention is a process for making a pharmaceutical composition comprising combining any of the compounds described above and a pharmaceutically acceptable carrier.

Further exemplifying the invention is the use of any of the compounds described above in the preparation of a medicament for the for the treatment of a disease or disorder which is dependent on the expression of a $T_3$ regulated gene or is associated with metabolic dysfunction. Still further exemplifying the invention is the use of any of the compounds described above in the preparation of a medicament for the for the treatment of obesity, hypercholesterolemia, atherosclerosis, depression, osteoporosis, hypothyroidism, goiter, thyroid cancer, glaucoma, cardiac arrhythmia, congestive heart failure, or skin disorders.

Further exemplifying the invention is the use of any of the compounds described above in the preparation of a medicament for the for the treatment of a skin disease or skin disorder. Said skin disease or disorder could be dermal atrophy such as glucocorticoid induced dermal atrophy, including restoration of dermal atrophy induced by topical glucocorticoids, the prevention of dermal atrophy induced by topical glucocorticoids (such as the simultaneous treatment with topical glucocorticoid or a pharmacological product including both glucocorticoid and a compound of the invention), the restoration/prevention of dermal atrophy induced by systemic treatment with glucocorticoids, restoration/prevention of atrophy in the respiratory system induced by local treatment with glucocorticoids, UV-induced dermal atrophy, or dermal atrophy induced by aging (wrinkles, etc.), wound healing, keloids, stria, cellulite, roughened skin, actinic skin damage, lichen planus, ichtyosis, acne, psoriasis, Dernier's disease, eczema, atopic dermatitis, chloracne, pityriasis and skin scarring.

The following definitions apply to the terms as used throughout this specification, unless otherwise limited in specific instances.

The term "thyroid receptor ligand" as used herein is intended to cover any chemical substance which binds to a thyroid receptor. The ligand may act as an antagonist, an agonist, a partial antagonist or a partial agonist.

The term "alkyl" as employed herein alone or as part of another group refers to acyclic straight or branched chain radical, containing 1 to 20 carbons, preferable 1 to 10 carbons in the normal chain, i.e. methyl, ethyl, propyl, propyl, butyl, pentyl, hexyl, heptyl, octyl, nonyl, docyl. Alkyl also includes a straight or branched alkyl group which contains or is interrupted by a cycloalkane, cycloalkene, aryl or heteroaryl ring, preferable 5 or 6 membered rings, saturated or unsaturated, as exemplified below:

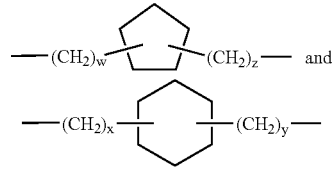

Wherein: when w and z=1 to 14, the sum of w and z is not more than 15; and when x and y=1 to 13, the sum of x and y is not more than 14. The alkyl portions can be attached at any variable point of attachment to the 5 or 6 membered ring. Alkyl also includes a straight or branched alkyl chain which is terminated at one, two or three points of substitution by a cycloalkane, cycloalkene, aryl or heteroaryl ring, preferable 5 or 6 membered rings, saturated or unsaturated, as exemplified below:

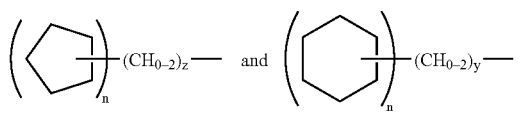

Wherein when n is 1, then z is=1 to 15 and y is=1 to 14; when n is 2, then z is=1 to 10 and y is=1 to 8; when n is 3, then z is=1 to 5 and y is=1 to 2. When substituted alkyl is present, this refers to a straight or branched alkyl group, including a chain interrupted or terminated by a ring, as defined above, substituted with 1–3 groups of $R^a$, which groups may be the same or different at any available point, including above defined rings, as defined with respect to each variable.

The term "alkenyl" as used herein by itself or as part of another group refers to straight or branched chain radicals of 2 to 20 carbons and at least one carbon to carbon double bond. Preferably one to two carbon-to-carbon double bonds is present, and up to 5 carbon-to-carbon bonds may be present. Preferable 2 to 10 carbons are present in the normal chain radical, such as ethenyl, propenyl, butenyl, pentenyl, hexenyl, heptenyl, octenyl, decenyl, dodecenyl and the like. As described above with respect to the "alkyl", the straight or branched portion of the alkenyl group may be interrupted or terminated by a ring and optionally substituted by 1 to 3 $R^a$ which groups may be the same or different when a substituted alkenyl group is provided.

The term "alkynyl" as used herein by itself or as part of another group refers to straight or branched chain radicals of 2 to 20 carbons with at least one carbon-to-carbon triple bond. Preferably one carbon-to-carbon triple bond is present, and up to 5 carbon-to-carbon triple bonds may be present. Preferably 2 to 10 carbons are present in the normal chain, such as ethynyl, propynyl, butynyl, pentynyl, hexynyl, heptynyl, octynyl, decynyl, dodecynyl and the like. As described above with respect to "alkyl", the straight or branched portion of the alkynyl group may be interrupted or terminated by a ring and optionally substituted by 1 to 3 groups of $R^a$ which groups may be the same or different when a substituted alkynyl group is provided.

The term "cycloalkyl" as employed herein alone or as part of another group refers to saturated cyclic hydrocarbon groups or partially unsaturated cyclic hydrocarbon groups, independently containing 1 to 2 carbon to carbon double bonds or carbon to carbon triple bonds. The cyclic hydrocarbon contain 3 to 15 carbons, including rings that are fused. It should also be understood that the present invention also involve cycloalkyl rings where 1 to 2 carbons in the ring are replaced by either —O—, —S— or —N—, thus forming a saturated or partially saturated heterocycle. Examples of such rings are piperidine, piperazine, morpholine, thiomorpholine, pyrrolidine, oxazolidine, thiazolidine, tetrahydrofurane, tetrahydrothiophene and the like. Preferred heterocyclic rings are 5- or 6-membered, which may be optionally substituted by 1 to 3 groups of $R^a$ which groups may be the same or different through available carbons as in the case of "alkyl". Preferred cycloalkyl groups include 3 to 7 carbons, such as cyclopropyl, cyclobutyl, cyclopentyl, cyclohexyl, cycloheptyl, which may be optionally substituted by 1 to 3 groups of $R^a$ which groups may be the same or different through available carbons as in the case of "alkyl".

The term "aryl" as employed herein alone or as part of another group refers to monocyclic, bicyclic and tricyclic aromatic groups, consisting of 6 to 15 carbons in the ring portion, including partially saturated rings as indanyl and tetrahydronaphthyl. The preferred aryl groups are phenyl and naphthyl, which may be substituted with 1 to 3 groups selected from $R^b$ which groups may be the same or different.

The term "halogen" refers to fluorine, chlorine, bromine and iodine. When $R_2$ is selected from alkyl, and is substituted with 1–3 groups of $R^b$ which groups may be the same or different, the preferred substitution include fluorine, thus forming substituents such as —$CF_3$ and —$CHF_2$.

The term "alkoxy" as employed herein alone or as part of another group refers to those groups of the designated carbon length in either a straight or branched configuration attached through an oxygen linkage and if two or more carbons in length, they may incude a double or a triple bond. Examples of such alkoxy groups are methoxy, ethoxy, propoxy, allyloxy, propargyloxy, butoxy, isobutoxy, tertiary butoxy, and the like.

The term "thio" as used herein as a part of another group, exemplified by "alkylthio" or "arylthio", refers to a carbon-sulphur-carbon bond and may also include higher oxidation states of sulphur, such as sulfoxides —SO— and sulphones —$SO_2$—.

The term "heteroaryl" or as used herein alone or as a part of another group refers to a group containing 5 to 15 atoms, where the aromatic ring includes 1, 2, 3 or 4 heteroatoms, as nitrogen, oxygen or sulfur. Such rings may be fused to another aryl or heteroaryl ring, and includes possible N-oxides. The heteroaryl group may optionally be substituted by the available carbons with 1 to 3 substituents of $R^b$ which groups may be the same or different.

When $R_1$ and $R^a$ is selected from heterocycles it refers to mainly to 5 to 9 membered rings, including fused rings thereof.

The term "phosphonic acid" and "phosphamic acid" refers to a phosphorus containing group of the structures:

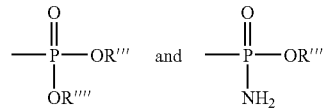

Wherein R''' and R'''' are independently selected from hydrogen, $C_{1-4}$ alkyl, $C_{2-4}$ alkenyl, or $C_{2-4}$ alkynyl.

The term "bioisosteric equivalent" refers to compounds or groups that possess near equal molecular shapes and volumes, approximately the same distribution of electrons, and which exhibit similar physical and biological properties. Examples of such equivalents are: (i) fluorine vs. hydrogen, (ii) oxo vs. thia, (iii) hydroxyl vs. amide, (iv) carbonyl vs. oxime, (v) carboxylate vs. tetrazole. Examples of such bioisosteric replacements can be found in the literature and examples of such are: (i) Burger A, *Relation of chemical structure and biological activity;* in Medicinal Chemistry Third ed., Burger A, ed.; Wiley-Interscience; New York, 1970, 64–80; (ii) Burger, A.; "Isosterism and bioisosterism in drug design"; *Prog. Drug Res.* 1991, 37, 287–371; (iii) Burger A, "Isosterism and bioanalogy in drug design", *Med. Chem. Res.* 1994, 4, 89–92; (iv) Clark R D, Ferguson A M, Cramer R D, "Bioisosterism and molecular diversity", *Perspect. Drug Discovery Des.* 1998, 9/10/11, 213–224; (v)

Koyanagi T, Haga T, "Bioisosterism in agrochemicals", *ACS Symp. Ser.* 1995, 584, 15–24; (vi) Kubinyi H, "Molecular similarities. Part 1. Chemical structure and biological activity", *Pharm. Unserer Zeit* 1998, 27, 92–106; (vii) Lipinski C A.; "Bioisosterism in drug design"; *Annu. Rep. Med. Chem.* 1986, 21, 283–91; (viii) Patani G A, LaVoie E J, "Bioisosterism: A rational approach in drug design", *Chem. Rev.* (Washington, D.C.) 1996, 96, 3147–3176; (ix) Soskic V, Joksimovic J, "Bioisosteric approach in the design of new dopaminergic/serotonergic ligands", *Curr. Med. Chem.* 1998, 5, 493–512 (x) Thornber C W, "Isosterism and molecular modification in drug design", *Chem. Soc. Rev.* 1979, 8, 563–80.

The compounds of formula I can be present as salts, in particular "pharmaceutically acceptable salts". A compound having at least one acid group (for example —COOH) can form salts with bases. Suitable salts with bases are, for example, metal salts, such as alkali metal or alkaline earth metal salts, for example sodium, potassium or magnesium salts, or salts with ammonia or an organic amine, such as morpholine, thiomorpholine, piperidine, pyrrolidine, a mono, di or trilower alkylamine, for example ethyl, tertbutyl, diethyl, diisopropyl, triethyl, tributyl or dimethyl-propylamine, or a mono, di or trihydroxy lower alkylamine, for example mono, di or triethanolamine. Corresponding internal salts may furthermore be formed. Preferred salts of the compounds of formula I include sodium, potassium and magnesium salts and pharmaceutically acceptable organic amines. The compounds of formula I having at least one basic center (for example —NH— in piperidine) can also form acid addition salts. These are formed, for example, with strong inorganic acids, such as mineral acids, for example sulfuric acid, phosphoric acid or a hydrohalic acid, with strong organic carboxylic acids, such as alkanecarboxylic acids of 1 to 4 carbon atoms which are unsubstituted or substituted, for example, by halogen, for example acetic acid, such as saturated or unsaturated dicarboxylic acids, for example oxalic, malonic, succinic, maleic, fumaric, phthalic or terephthalic acid, such as hydroxycarboxylic acids, for example ascorbic, glycolic, lactic, malic, tartaric or citric acid, such as amino acids, (for example aspartic or glutamic acid or lysine or arginine), or benzoic acid, or with organic sulfonic acids, such as ($C_1$–$C_4$) alkyl or arylsulfonic acids which are unsubstituted or substituted, for example by halogen, for example methyl- or p-toluene-sulfonic acid. Corresponding acid addition salts can also be formed having, if desired, an additionally present basic center. Salts which are unsuitable for pharmaceutical uses but which can be employed, for example, for the isolation or purification of free compounds I or their pharmaceutically acceptable salts, are also included.

Preferred salts of the compounds of formula I which include an acid group include sodium, potassium and magnesium salts and pharmaceutically acceptable organic amines.

Preferred salts of the compounds of formula I which include a basic groups include monohydrochloride, hydrogensulfate, methanesulfonate, phosphate or nitrate.

An acid center (for example —COOH) part in formula I can form "prodrug ester forms" known in the art such as pivaloyloxymethyl or dioxolenylmethyl. Such prodrug esters are described in standard references such as Chapter 31, written by Camille G. Wermuth et al., in "The Practice of Medicinal Chemistry", ed. C. G. Wermuth, Academic Press, 1996 (and the references contained therein).

Certain compounds of the invention can be "stereoisomers", which have one or more asymmetric centers and can exist in the form of racemates, single enantiomers, as individual diastereomers, with all possible isomers, and mixtures thereof, all of which are within the scope of the invention.

The compounds of formula I may be prepared by the exemplary processes described in the following reaction schemes. Exemplary reagents and procedures for these reactions appear hereinafter and in the working Examples. With respect to the reaction scheme below, although the various $R_1$, $R_2$, $R_3$, $R_4$, $R_5$, $R^a$, $R^b$, $R^c$, $R^d$ and n moieties sometimes are specifically defined, unless otherwise indicated, it is to be understood that $R_1$, $R_2$, $R_3$, $R_4$, $R_5$, $R^a$, $R^b$, $R^c$, $R^d$ may be any of the groups encompassed thereby and n may be 0, 1, 2, or 3.

Scheme 1 outlines a synthetic route which leads to the preparation of the intermediate aniline derivative 6, including several other key intermediates, used in the invention. Alternative synthetic routes to these compounds can be visualized by any person skilled in the art and the present synthetic route is not limiting for the invention. The synthetic route starts as depicted below, when a mixture of the appropriate phenol 2 and arylfluoride 1 is heated at reflux in a solvent as dimethyl-formamide, and in the presence of copper bronze and a base such as potassium carbonate. Other combinations of phenols, aryl halides, bases and solvents can be appropriate and are well known for those skilled in the art. The reaction mixture is purified by standard extraction procedures and recrystallization, to give biaryl ether 3 as an end product. Numerous other methods exist in the literature for the synthesis of diaryl ethers, for example, two references directly apply to the synthesis of thyroid hormone analogs: Evans D A et al., *Tetrahedron Lett.* 1998, 39, 2937–2940 and Salamonczyk G M et al., *Tetrahedron Lett.* 1997, 38, 6965–6968.

Application of Sonagashira coupling of aryhalide 3 with trimethylsilylacetylene, using standard conditions, gives the coupled product 4, which after desilylation and subsequent oxidation, employing an oxidant as hydrogen peroxide in the presence of base, gives phenylacetic acid 5. Standard re-esterfication give methyl ester 6. Other examples of direct or indirect transformation of an aryl halide to compounds wherein $R_5$ is COOH and n=0 to 3 in formula I include, but is not restricted to: (i) when n=0, alkoxycarbonylation of aryl halides performed under pressure of CO in the presence of for example a palladium or cobalt catalyst; (ii) when n=1, palladium-catalyzed coupling of the Reformatsky reagent with aryl halides; (iii) when n=2, Heck-couplings of aryl halides with alkyl acrylates, followed by reduction. The intermediate nitro product 6 is reduced by hydrogenation at 1–2 atmospheres of hydrogen in the presence of a catalyst such as platinum(II) oxide in an inert solvent such as ethylacetate at room temperature. Standard work-up and purification yields the desired aniline product 7. Other combinations of catalysts, solvent and hydrogen pressure, alternatively transfer hydrogenation, may be employed and are evident for those skilled in the art. But, with more active catalysts such as palladium on graphite, with increased pressures of hydrogen and/or higher temperatures, there is an increased risk of dehalogenation during catalytic hydrogenation. This is well documented in the litterature and some examples are: (i) Palladium/graphite, cyclohexene, Entwistle I D, Johnston R A W, Povall T J. *Chem. Soc. Perkin Trans.* 1975, 1, 1300; (ii) $H_2$, Pd/graphite methanol, Ishikawa F, Saegusa J, Inamura K, Sakuma K, Ashida S H I-I, *J. Med. Chem.* 1985, 28, 1387; (iii) Ammonium formate catalytic transfer hydrogenation, Anwer M K., Sherman D B, Roney J G, Spatola A F, *J. Org. Chem.* 1989, 54. Apart from catalytic hydrogenation and transfer hydrogenation several other methods exist that chemoselectively reduce aromatic nitro compounds in the presence of aromatic chlorines: (i) NaBH$_4$/SbCl$_3$ or NaBH$_4$/BiCl$_3$, Ren P D, Pan S F, Dong T W, Wu S H, *Synthetic commun.* 1995, 25, 3799–3803; (ii) (NH$_4$)$_2$SO$_4$—Mg/Al/Bi, Prajapati D, Borah H N, Sandhu J S, Ghosh A C, *Synthetic commun.* 1995, 25, 4025–4028; (iii) Wilkinsons Catalyst, Brinkman H R, Hilborn M D, Smith M C, Miles W H, *Synthetic Commun.* 1996, 26, 973–980; (iv) sodium dithionite, Khurana J M, Singh S J, *Indian Chem. Soc.* 1996, 73, 487–488; (v) Pictet-Spengler reaction in trifluoroacetic acid, Zhang L H, Meier W, Wats E, Costello T D, Ma P, *Tetrahedron Lett.* 1995, 36, 8387–8390; (vi) two phase system with water soluble palladium catalysts, Tafesh A M, Beller M, *Tetrahedron Lett.* 1995, 36, 9305–3908. It should be evident for those skilled in the art that several of the alternative methods above also might reduce carbonyl functions.

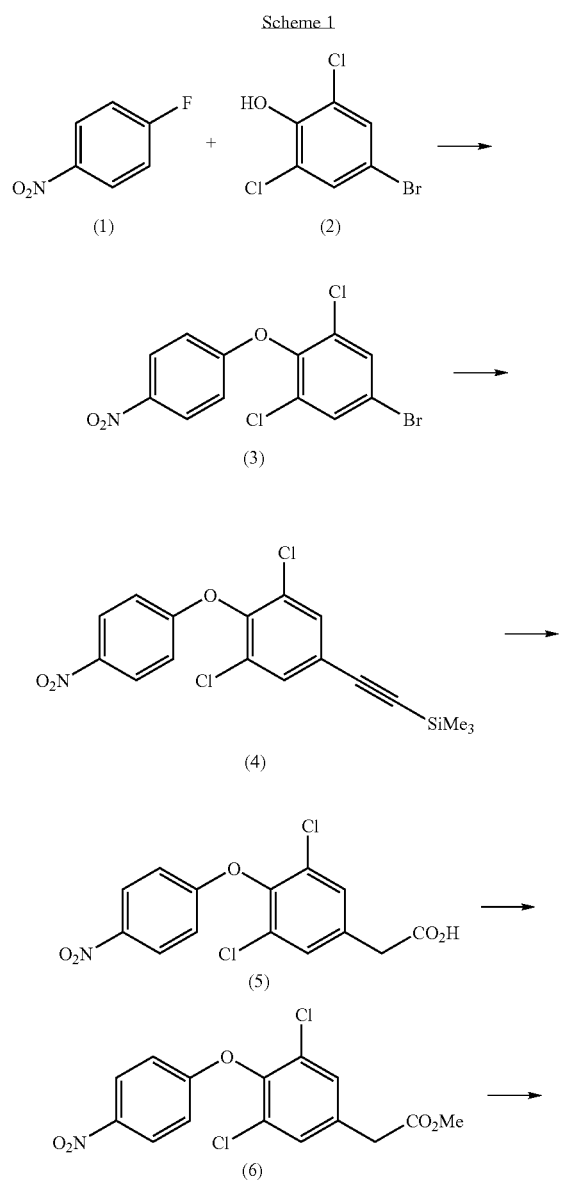

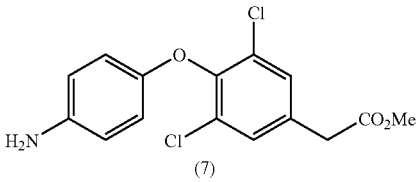

Examples of compounds of formula I in which intermediate 7 is coupled with an acid chloride or an anhydride to produce an amide is shown in Scheme 2.

In one procedure, a mixture of intermediate 7 and a base such as triethylamine in dichloromethane is stirred at room temperature. The appropriate acid chloride is added and the reaction mixture yields after work-up and purification by either chromatography or recrystallization the desired material. The carboxylic acid ester is removed with a mixture of a base such as aqueous sodium hydroxide and a solvent such as methanol. Acidification of the completed reaction mixture is followed by standard work-up and crystallization or chromatography, to yield the end product 9 (Example 2). Other protecting groups for the carboxylic acid can be employed, and their usage is known to those skilled in the art (references describing protecting group strategy include, for example, "*Protecting Groups in Organic Chemistry*", J. F. W. McOmie, Plenum Press, London, N.Y., 1973, and "*Protective Groups in Organic Synthesis*", T. W. Greene, Wiley, New York, 1984).

Various R$_2$-substituted phenoxy amides of formula I can be obtained from intermediate 7 in Scheme 2. For example, it can be regioselectively ortho-brominated by for example 2,4,4,6-tetrabromo-2,5-cyclohexadienone to give 10. Numerous other methodologies for bromination of aromatics to give the corresponding aryl bromide are well known to those skilled in the art. Intermediate 10 may then be acylated on the aniline group to provide a variety of substituted phenoxyamides wherein R$_2$=Br. Intermediate 11 in Scheme 2 may be further converted to compounds of formula I in which R$_2$ is aryl, alkenyl or alkyl by any one of a number of methods well known to those skilled in the art. Coupling of amines with any one of the methods described above give after removal of the carboxyl protecting group final products 12 (Examples 1, 4, 7, 16–18) and 14 (Example 3, 8, 15, 81). Several other related methodologies exist for the coupling of acid chlorides, anhydrides and sulfonyl chlorides with aromatic, as well as non-aromatic, amines in solution or solid phase and are known to those skilled in the art.

Amides can also be prepared by parallel solution phase synthesis to give the end products 9 and 12. In one procedure the appropriate carboxylic acid, a coupling reagent such as 3-ethyl-1-[3-(dimethylamino)propyl]carbodiimide hydrochloride, a base such as 1-hydroxybenzotriazole hydrate and an inert solvent such as dichloromethane is loaded in separate vessels. The amine 7 or 10 is added, the reaction mixture heated and the methyl ester function removed as described above to give the amide end-products (Examples 33, 37–47, 49, 52, 54, 57–61, 66–72).

In another modification of the same procedure as above, benzotriazole-1-yl-oxy-tris-pyrrolidino phosphonium hexafluorophosphate is added to the reaction vessel after 18 hours (Example 48, 50–51, 53, 62–65, 73–74).

Other combinations of base and coupling reagents can be employed here with successful results.

Scheme 2

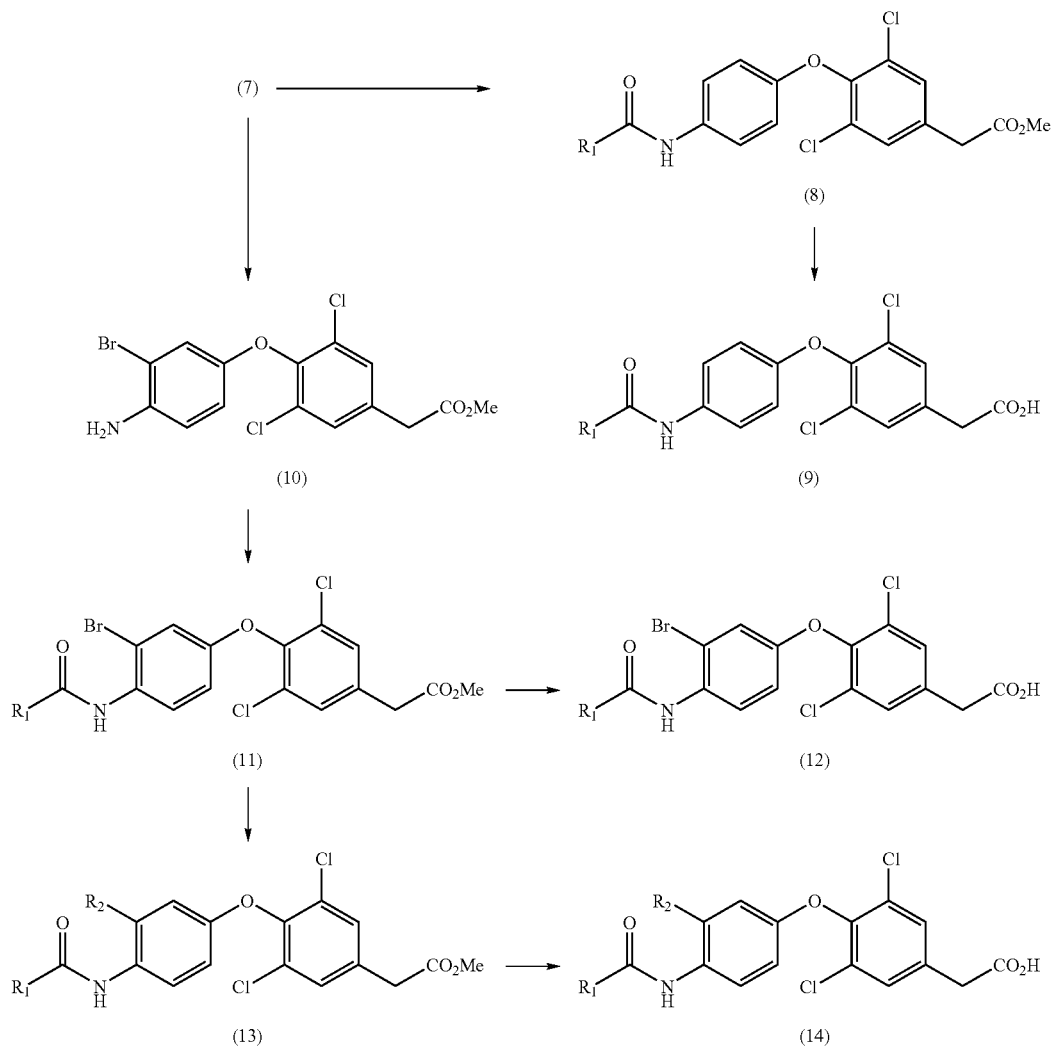

Alternative synthetic strategies for the preparation of Examples where $R_2$ is not hydrogen can be realized by those who are skilled in the art. For example, Scheme 3 shows how a $R_2$-substituent can be present prior the formation of the biaryl ether. Standard coupling procedures, as described above, might involve any substitution at the $R_2$-position. In one example, intermediate 15 is coupled with intermediate 16 to give biaryether 17. Standard transformations as described above gives the end-products 18, where $R_2=CF_3$ (Example 19).

Scheme 3

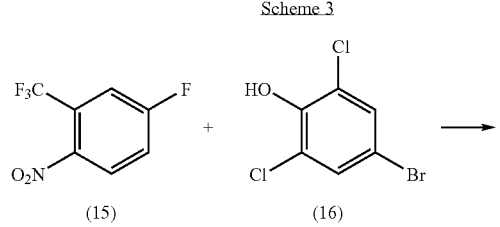

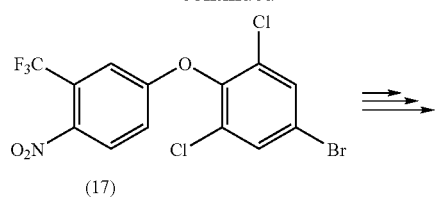

Example 19, $R_1$ = i-Pr

In another example of an alternative strategy, amide 8 can be substituted at the $R_2$-position by aromatic electrophilic substitution, using any one of the methods described in for example "*Advanced Organic Chemistry*", 4th edition, Jerry March, Wiley-Interscience publication, 1992, p 521–568, including references cited therein. In one example, 8 is regioselectively ortho-chlorinated by tert-butyl hypochorite. Standard hydrolysis, as described above, gives the end product 19. Several other methods of chlorination of amides and anilines, without involving chlorine gas, are known in the literature and might be used here with successful results: (i) Benzyltrimethylammonium tetrachloroiodate, S Kajigaeshi et al, *Bull. Chem. Soc. Jpn,* 1989, 62, 2096–2098; (ii) Calcium hypochlorite, S O Nwaukwa and P M Keehn, *Synthetic Commun.,* 1989, 19(5&6), 799–804; (iii) Sulphuryl chloride, Jones T R, Smithers M J, Taylor M A., Jackman A L, Calvert A H, Harland S J, Harrap K R, *J. Med. Chem.,* 1986, 29, 468–472; and the like.

Scheme 4

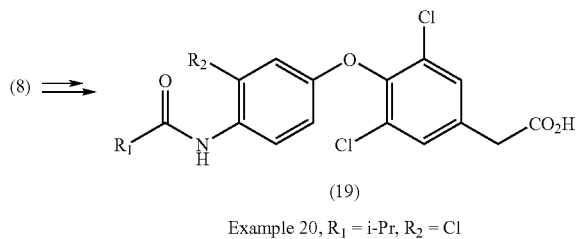

(19)

Example 20, $R_1$ = i-Pr, $R_2$ = Cl

A library of sulphonamides can also be prepared by parallel solution phase synthesis (Examples 34, 55–56, 75–80). In one exemplified procedure the appropriate sulfonyl chloride, a base such as pyridine and an inert solvent as dichloromethane is loaded in separate vessels. The amine 7 is added, the reaction mixture heated and the methyl ester function removed as described above to give the sulphonamide end-products 20.

Scheme 5

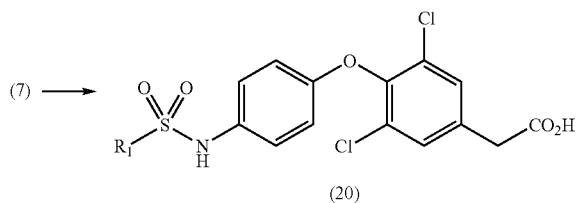

(20)

Examples of compounds of formula I in which -Q-NH— is equivalent to a substituted urea or thiourea is showed in Scheme 6. In one exemplified procedure the appropriate isocyanate is solved in an inert solvent such as dichloromethane. The amine 7 is added, the reaction mixture heated and the methyl ester function removed as described above to give the end-products 21 (Examples 35–36).

Scheme 6

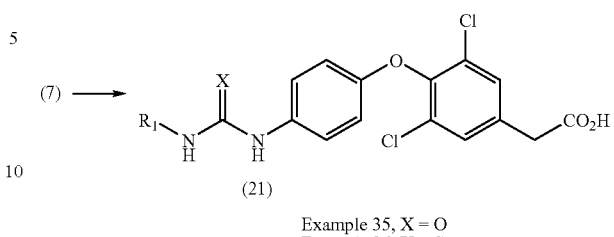

(21)

Example 35, X = O
Example 36, X = S

Examples of compounds of formula I in which $R_5$ is an amide produced by coupling to an amino acid are shown in Scheme 7. The following procedure involve the coupling of an acetic acid derivative such as 9 or 12, with protected amino acids, to afford after any necessary protecting removal the corresponding amides 22. The procedure might also be applied for the preparation of compounds of formula I, where n=0, 2 or 3. In one exemplified procedure, a mixture of compound 9, a coupling reagent such as 3-ethyl-1-[3-(dimethylamino)-propyl]carbodiimide hydrochloride, and a base such as 1-hydroxybenzotriazole hydrate in dimethylformamide is stirred at room temperature. The appropriate protected amino acid and triethylamine is added. The reaction mixture yields after work-up and purification by either chromatography or recrystallization the corresponding coupled material, which after the removal of protecting groups, gives the desired final amide products 22 (Example 9–14). The R' groups in the examples should not be seen as limiting, but may also be any of the side chains found in the naturally occurring alpha-amino acids and their analogs. Numerous other related methodologies exist for the coupling of amino acids with aromatic, as well as non-aromatic, carboxylic acids in solution or solid phase and are known to those skilled in the art.

Scheme 7

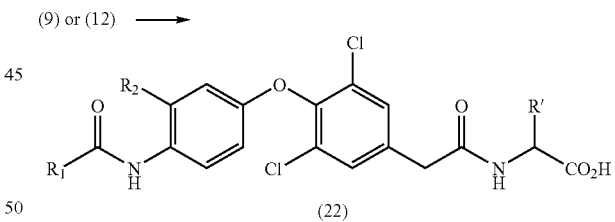

(22)

Scheme 8 depicts a synthesis of compounds of formula I in which $R_5$=COOH and is connected to the aromatic ring by an intervening double bond (alkenyl carboxylic acid) or a —$CH_2CH_2$— group. Reaction of diaryl ether 3 with an acrylate ester such as ethyl acrylate, using palladium acetate, triphenyl phosphine and triethylamine in a solvent such as acetonitrile with heating at elevated temperatures gives a cinnamate ester product 23. The double bond can be reduced to the saturated analogue 26, alternatively ortho-brominated by the methods described previously. After reduction of the nitro group to an amine and coupling with an acylhalide and subsequent removal of the ester as described above, alkenyl carboxylic acid 25 and propionic acid 27 is obtained (Example 22–28).

Scheme 8

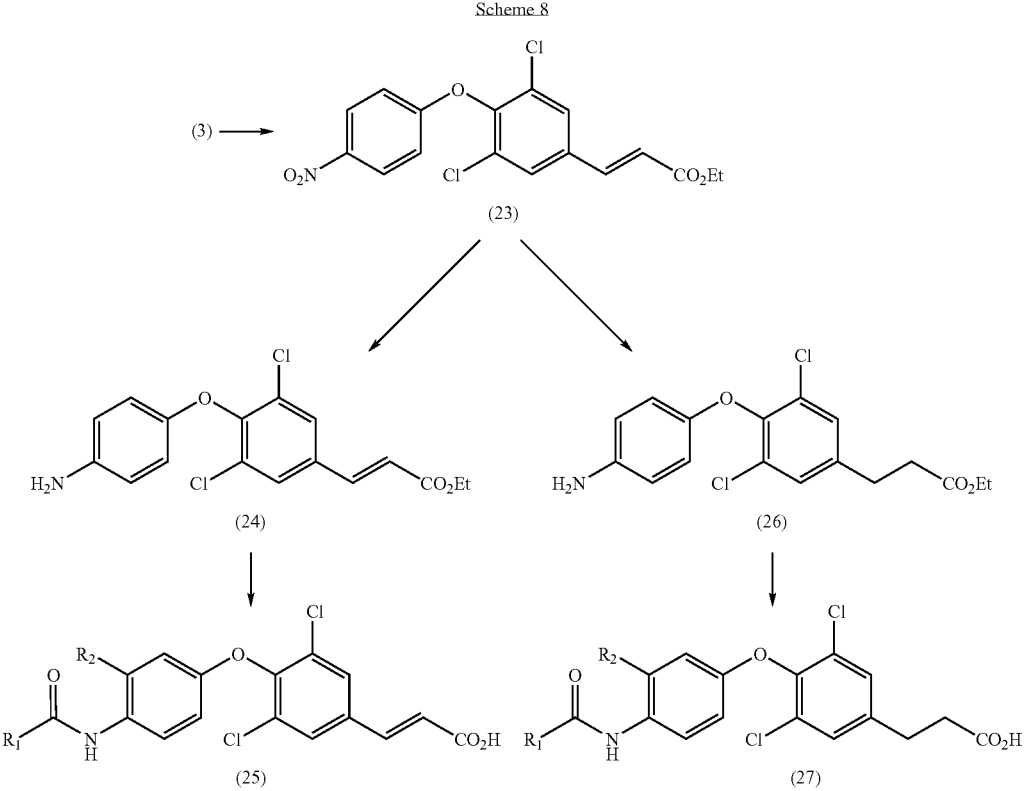

Schemes 9 and 10 outline several alternative procedures for the preparation of analogues where the $R_1$ substituent is connected with the $R_2$ substituent via the available carbons, thus forming a 5 or 6 membered aza containing heterocyclic ring.

In scheme 9 internal Heck-coupling of intermediate 28, employing standard conditions, gives the oxindole 29, were $R^c$=isopropylidene subsequently can be reduced to $R^c$=isopropyl. As well known to those skilled in the art, the palladium catalyzed coupling might also involve palladium insertion at iodine, triflate, mesylate and the like, followed by cyclization. By the provided method, alternative groups of $R^c$ is possible and might include, but is not restricted to, alkyl, alkenyl and the like. As an alternative method, internal Friedel-crafts alkylation of intermediate 30, employing standard conditions, can give substituted oxindoles. As known to those skilled in the art, a multitude of different reaction conditions, reactants and catalysts can be used in Friedel-crafts alkylations, and several exhaustive review articles on the topic can be found in the litterature. Compared with above, the method provide additional opportunities for the variation of $R^c$.

Scheme 9

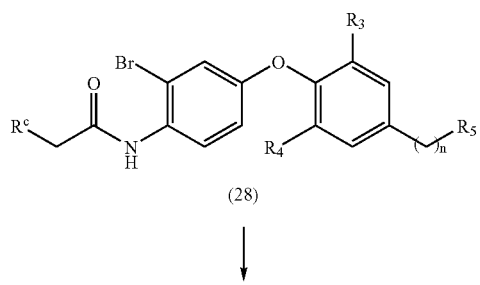

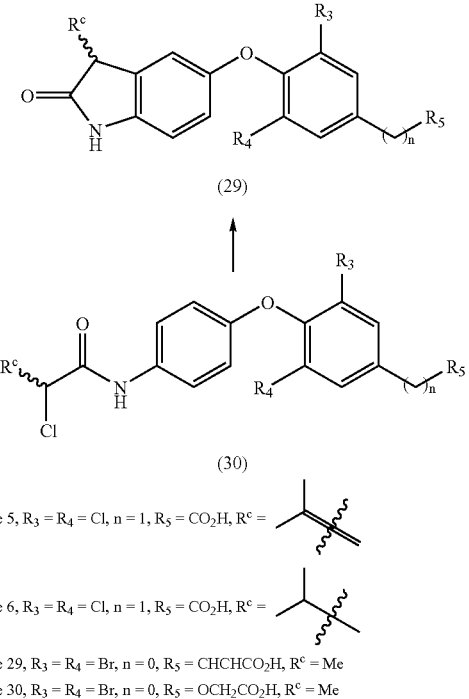

Example 5, $R_3 = R_4 = Cl$, $n = 1$, $R_5 = CO_2H$, $R^c = $

Example 6, $R_3 = R_4 = Cl$, $n = 1$, $R_5 = CO_2H$, $R^c = $

Example 29, $R_3 = R_4 = Br$, $n = 0$, $R_5 = CHCHCO_2H$, $R^c = Me$
Example 30, $R_3 = R_4 = Br$, $n = 0$, $R_5 = OCH_2CO_2H$, $R^c = Me$ In scheme 10, methods for the preparation of rings with two heteroatoms are depicted. Intermediates 31 and 33 were prepared by standard methods from available starting materials. When intermediate 31 is reacted under basic conditions with an alicyclic compound containing two reaction centers, such as chloroacetyl chloride, the corresponding 1,4-benzoxazine 32 is obtained. This is followed by standard work-up and subsequent hydrolyzis. The corresponding imidazolinone, can be prepared when diamino compound 33 is reacted with N,N'-disuccinimidyl carbonate in a solvent such as acetonitrile. Several alternative combinations of reactants and solvents, for the preparation of heterocyclic rings, are evident for those skilled in the art.

substantially pure form. The compounds of the present invention can have asymmetric centers at any of the carbon atoms including any one of the R substituents. Consequently, compounds of formula I can exist in enantiomeric or diastereomeric forms or in mixtures thereof. The process for separation can utilize racemates, enantiomers or diastereomers as starting materials. When diastereomeric or enantiomeric products are prepared, they can be separated by conventional methods, for example, by chromatographic means or by fractional crystallization.

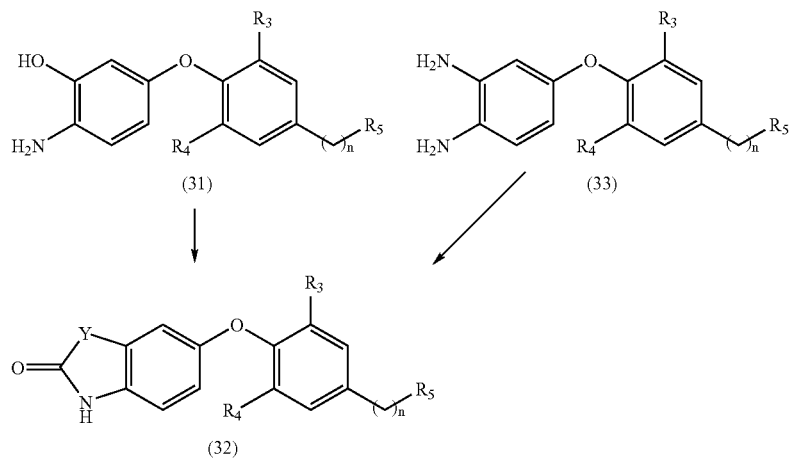

Example 21, $R_3 = R_4 = Cl$, $n = 1$, $R_5 = CO_2H$, $Y = NH$
Example 32, $R_3 = R_4 = i\text{-}Pr$, $n = 2$, $R_5 = CO_2H$, $Y = CH_2O$ Scheme 11 depicts a synthesis of compounds of formula I in which Z is —$(CH_2)_n$—, n=0 and $R_5$ is an acylsulfonamide (—$CONHSO_2R'$). In one exemplified procedure, a mixture of intermediate 12, a coupling reagent such as 3-ethyl-1-[3-(dimethylamino)propyl]carbodiimide hydrochloride (EDCI), and a base such as dimethylaminopyridine (DMAP) and the appropriate sulphon-amide in dichloromethane is stirred at room temperature. The reaction mixture yields after work-up and appropriate purification the corresponding coupled material 33 (Example 31). Several other combinations of base and coupling reagent can be applied and is well known to those skilled in the art. Also, other sulphonamides can be used in the present procedure to prepare further ligands which are sulphonamides.

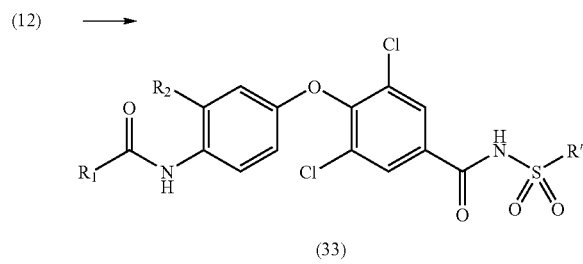

Example 31, $R_1 = i\text{-}Pr$, $R_2 = Cl$, $R' = Ph$

All stereoisomers of the compounds of the instant invention are contemplated, either in admixture or in pure or The compounds of the invention are agonists, that preferably may be selective for the thyroid hormone receptor-beta, and as such are useful in the treatment of obesity, hypercholesterolemia and atherosclerosis by lowering of serum LDL levels, alone or in combination with a lipid modulating drug such as an HMG-CoA reductase inhibitor, fibrate, thiazolidinedione, or MTP inhibitor, amelioration of depression alone or in combination with an antidepressant, and stimulation of bone formation to treat osteoporosis in combination with any known bone resorption inhibitor such as alendronate sodium. In addition, the compounds of the invention may be useful as replacement therapy in elderly patients with hypothyroidism or subclinical hypothyroidism who are at risk for cardiovascular complications, in the treatment of the elderly to provide a sense of well-being, and in the treatment of non-toxic goiter; in the management of papillary or follicular thyroid cancer (alone or with $T_4$); in the treatment of skin disorders such as psoriasis, glaucoma, cardiovascular disease such as in the prevention or treatment of atherosclerosis, and congestive heart failure.

The compounds of the invention may be employed alone or in combination with an appetite suppressant such as sibutramine, and/or in combination with anti-obesity agents such as orlistat, and/or in combination with a b3 agonist, for treating obesity.

The compounds of the invention may also be used to treat skin disorders or diseases involving dermal atrophy such as glucocorticoid induced dermal atrophy, including restoration of dermal atrophy induced by topical glucocorticoids, the prevention of dermal atrophy induced by topical glucocorticoids (such as the simultaneous treatment with topical glucocorticoid or a pharmacological product including both glucocorticoid and a compound of the invention), the restoration/prevention of dermal atrophy induced by systemic treatment with glucocorticoids, restoration/prevention of atrophy in the respiratory system induced by local treatment with glucocorticoids, UV-induced dermal atrophy, or dermal atrophy induced by aging (wrinkles, etc.), wound healing, keloids, stria, cellulite, roughened skin, actinic skin damage, lichen planus, ichtyosis, acne, psoriasis, Dernier's disease, eczema, atopic dermatitis, chloracne, pityriasis and skin scarring.

In treating skin disorders or diseases as described above, the compounds of the invention may be used alone or optionally in combination with a retinoid such as tretinoin or a vitamin D analog, employing amounts as disclosed in the PDR.

The hypolipidemic agent which may be optionally employed in combination with the compounds of formula I of the invention may include thiazolidinediones, MTP inhibitors, HMG CoA reductase inhibitors, squalene synthetase inhibitors, fibric acid derivatives, ACAT inhibitors, cholesterol absorption inhibitors, ileal $Na^+$/bile acid cotransporter inhibitors, bile acid sequestrants, and/or nicotinic acid and derivatives thereof.

MTP inhibitors employed herein include MTP inhibitors disclosed in U.S. Pat. Nos. 5,595,872, 5,739,135, 5,712,279, 5,760,246, 5,827,875, 5,885,983 and U.S. application Ser. No. 09/175,180 filed Oct. 20, 1998, now U.S. Pat. No. 5,962,440. Preferred are each of the preferred MTP inhibitors disclosed in each of the above patents and applications.

All of the above U.S. patents and applications are incorporated herein by reference.

Most preferred MTP inhibitors to be employed in accordance with the present invention include preferred MTP inhibitors as set out in U.S. Pat. Nos. 5,739,135 and 5,712,279, and 5,760,246.

The most preferred MTP inhibitor is
9-[4-[4-[[2-(2,2,2-Trifluoroethoxy)benzoyl]amino]-1-piperidinyl]butyl]-N-(2,2,2-trifluoroethyl)-9H-fluorene-9-carboxamide:

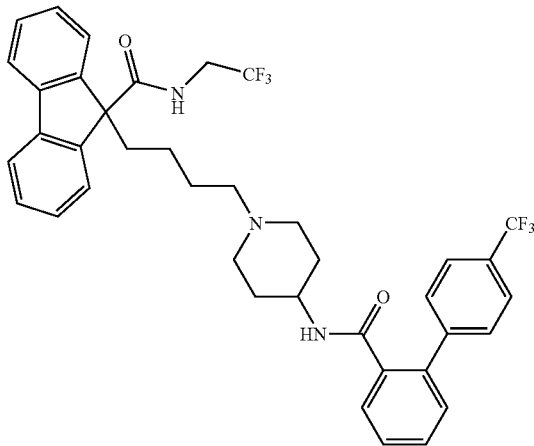

The hypolipidemic agent may be an HMG CoA reductase inhibitor which includes, but is not limited to, mevastatin and related compounds as disclosed in U.S. Pat. No. 3,983,140, lovastatin (mevinolin) and related compounds as disclosed in U.S. Pat. No. 4,231,938, pravastatin and related compounds such as disclosed in U.S. Pat. No. 4,346,227, simvastatin and related compounds as disclosed in U.S. Pat. Nos. 4,448,784 and 4,450,171. Other HMG CoA reductase inhibitors which may be employed herein include, but are not limited to, fluvastatin, disclosed in U.S. Pat. No. 5,354,772, cerivastatin disclosed in U.S. Pat. Nos. 5,006,530 and 5,177,080, atorvastatin disclosed in U.S. Pat. Nos. 4,681,893, 5,273,995, 5,385,929 and 5,686,104, pyrazole analogs of mevalonolactone derivatives as disclosed in U.S. Pat. No. 4,613,610, indene analogs of mevalonolactone derivatives as disclosed PCT application WO 86/03488, 6-[2-(substituted-pyrrol-1-yl)-alkyl)pyran-2-ones and derivatives thereof as disclosed in U.S. Pat. No. 4,647,576, Searle's SC-45355 (a 3-substituted pentanedioic acid derivative) dichloroacetate, imidazole analogs of mevalonolactone as disclosed in PCT application WO 86/07054, 3-carboxy-2-hydroxy-propane-phosphonic acid derivatives as disclosed in French Patent No. 2,596,393, 2,3-disubstituted pyrrole, furan and thiophene derivatives as disclosed in European Patent Application No. 0221025, naphthyl analogs of mevalonolactone as disclosed in U.S. Pat. No. 4,686,237, octahydronaphthalenes such as disclosed in U.S. Pat. No. 4,499,289, keto analogs of mevinolin (lovastatin) as disclosed in European Patent Application No. 0,142,146 A2, as well as other known HMG CoA reductase inhibitors.

In addition, phosphinic acid compounds useful in inhibiting HMG CoA reductase suitable for use herein are disclosed in GB 2205837.

The squalene synthetase inhibitors suitable for use herein include, but are not limited to, a-phosphono-sulfonates disclosed in U.S. Pat. No. 5,712,396, those disclosed by Biller et al, J. Med. Chem., 1988, Vol. 31, No. 10, pp 1869–1871, including isoprenoid (phosphinylmethyl)phosphonates as well as other squalene synthetase inhibitors as disclosed in U.S. Pat. Nos. 4,871,721 and 4,924,024 and in Biller, S. A., Neuenschwander, K., Ponpipom, M. M., and Poulter, C. D., Current Pharmaceutical Design, 2, 1–40 (1996).

In addition, other squalene synthetase inhibitors suitable for use herein include the terpenoid pyrophosphates disclosed by P. Ortiz de Montellano et al, J. Med. Chem., 1977, 20, 243–249, the farnesyl diphosphate analog A and presqualene pyrophosphate (PSQ-PP) analogs as disclosed by Corey and Volante, J. Am. Chem. Soc., 1976, 98, 1291–1293, phosphinylphosphonates reported by McClard, R. W. et al, J.A.C.S., 1987, 109, 5544 and cyclopropanes reported by Capson, T. L., PhD dissertation, June, 1987, Dept. Med. Chem. U of Utah, Abstract, Table of Contents, pp 16, 17, 40–43, 48–51, Summary.

Other hypolipidemic agents suitable for use herein include, but are not limited to, fibric acid derivatives, such as fenofibrate, gemfibrozil, clofibrate, bezafibrate, ciprofibrate, clinofibrate and the like, probucol, and related compounds as disclosed in U.S. Pat. No. 3,674,836, probucol and gemfibrozil being preferred, bile acid sequestrants such as cholestyramine, colestipol and DEAE-Sephadex (Secholex®, Policexide®), as well as lipostabil (Rhone-Poulenc), Eisai E-5050 (an N-substituted ethanolamine derivative), imanixil (HOE-402), tetrahydrolipstatin (THL), istigmastanylphos-phorylcholine (SPC, Roche), aminocyclodextrin (Tanabe Seiyoku), Ajinomoto AJ-814 (azulene derivative), melinamide (Sumitomo), Sandoz 58-035, American Cyanamid CL-277,082 and CL-283,546 (disubstituted urea derivatives), nicotinic acid, acipimox, acifran, neomycin, p-aminosalicylic acid, aspirin, poly(diallylmethylamine) derivatives such as disclosed in U.S. Pat. No. 4,759,923, quaternary amine poly(diallyldimethylammonium chloride) and ionenes such as disclosed in U.S. Pat. No. 4,027,009, and other known serum cholesterol lowering agents.

The other hypolipidemic agent may be an ACAT inhibitor such as disclosed in, Drugs of the Future 24, 9–15 (1999), (Avasimibe); "The ACAT inhibitor, C1-1011 is effective in the prevention and regression of aortic fatty streak area in hamsters", Nicolosi et al, Atherosclerosis (Shannon, Irel). (1998), 137(1), 77–85; "The pharmacological profile of FCE 27677: a novel ACAT inhibitor with potent hypolipidemic activity mediated by selective suppression of the hepatic secretion of ApoB100-containing lipoprotein", Ghiselli, Giancarlo, Cardiovasc. Drug Rev. (1998), 16(1), 16–30; "RP 73163: a bioavailable alkylsulfinyl-diphenylimidazole ACAT inhibitor", Smith, C., et al, Bioorg. Med. Chem. Lett. (1996), 6(1), 47–50; "ACAT inhibitors: physiologic mechanisms for hypolipidemic and anti-atherosclerotic activities in experimental animals", Krause et al, Editor(s): Ruffolo, Robert R., Jr.; Hollinger, Mannfred A., Inflammation: Mediators Pathways (1995), 173–98, Publisher: CRC, Boca Raton, Fla.; "ACAT inhibitors: potential anti-atherosclerotic agents", Sliskovic et al, Curr. Med. Chem. (1994), 1(3), 204–25; "Inhibitors of acyl-CoA:cholesterol O-acyl transferase (ACAT) as hypocholesterolemic agents. 6. The first water-soluble ACAT inhibitor with lipid-regulating activity. Inhibitors of acyl-CoA:cholesterol acyltransferase (ACAT). 7. Development of a series of substituted N-phenyl-N'-[(1-phenylcyclopentyl)methyl]ureas with enhanced hypocholesterolemic activity", Stout et al, Chemtracts: Org. Chem. (1995), 8(6), 359–62.

The hypolipidemic agent may be a cholesterol absorption inhibitor preferably Schering-Plough's SCH48461 as well as those disclosed in Atherosclerosis 115, 45–63 (1995) and J. Med. Chem. 41, 973 (1998).

The hypolipidemic agent may be an ileal $Na^+$/bile acid cotransporter inhibitor such as disclosed in Drugs of the Future, 24, 425–430 (1999).

Preferred hypolipidemic agents are pravastatin, lovastatin, simvastatin, atorvastatin, fluvastatin and cerivastatin.

The above-mentioned U.S. patents are incorporated herein by reference. The amounts and dosages employed will be as indicated in the Physician's Desk Reference and/or in the patents set out above.

The compounds of formula I of the invention will be employed in a weight ratio to the hypolypidemic agent, the antidepressant, and/or bone resorption inhibitor and/or appetite suppressant (where present), within the range from about 500:1 to about 0.005:1, preferably from about 300:1 to about 0.01:1.

The antidiabetic agent which may be optionally employed in combination with compounds of formula I of the invention may include biguanides, sulfonyl ureas, glucosidase inhibitors, thiazolidinediones and/or aP2 inhibitors and/or PPAR a agonists, PPAR g agonists or PPAR a/g dual agonists, and/or SGLT2 inhibitors, or meglitimide.

The antidiabetic agent may be an oral antihyperglycemic agent preferably a biguanide such as metformin or phenformin or salts thereof.

Where the antidiabetic agent is a biguanide, the compounds of structure I will be employed in a weight ratio to biguanide within the range from about 0.01:1 to about 100:1, preferably from about 0.5:1 to about 2:1.

The antidiabetic agent may also preferably be a sulfonylurea such as glyburide (also known as glibenclamide), glimepiride (disclosed in U.S. Pat. No. 4,379,785), glipizide, gliclazide or chlorpropamide, other known sulfonylureas or other antihyperglycemic agents which act on the ATP-dependent channel of the b-cells, with glyburide and glipizide being preferred.

The compounds of structure I will be employed in a weight ratio to the sulfonyl urea in the range from about 0.01:1 to about 100:1, preferably from about 0.2:1 to about 10:1.

The oral antidiabetic agent may also be a glucosidase inhibitor such as acarbose (disclosed in U.S. Pat. No. 4,904,769) or miglitol (disclosed in U.S. Pat. No. 4,639,436), which may be administered in a separate oral dosage form.

The compounds of structure I will be employed in a weight ratio to the glucosidase inhibitor within the range from about 0.01:1 to about 100:1, preferably from about 0.5:1 to about 50:1.

The compounds of structure I may be employed in combination with a thiazolidinedione oral anti-diabetic agent or other insulin sensitizers (which has an insulin sensitivity effect in NIDDM patients) such as troglitazone (Warner-Lambert's Rezulin®, disclosed in U.S. Pat. No. 4,572,912), rosiglitazone (SKB), pioglitazone (Takeda), Mitsubishi's MCC-555 (disclosed in U.S. Pat. No. 5,594,016), Glaxo-Welcome's GI-262570, englitazone (CP-68722, Pfizer), or darglitazone (CP-86325, Pfizer).

The compounds of structure I will be employed in a weight ratio to the thiazolidinedione in an amount within the range from about 0.01:1 to about 100:1, preferably from about 0.5:1 to about 5:1.

The sulfonylurea and thiazolidinedione in amounts of less than about 150 mg oral antidiabetic agent may be incorporated in a single tablet with the compounds of structure I.

The compounds of structure I may also be employed in combination with a non-oral antihyperglycemic agent such as insulin or with glucagon-like peptide-1 (GLP-1) such as GLP-1(1-36) amide, GLP-1(7-36) amide, GLP-1(7-37) (as disclosed in U.S. Pat. No. 5,614,492 to Habener, the disclosure of which is incorporated herein by reference), which may be administered via injection, intranasal, or by transdermal or buccal devices.

Where present, metformin, the sulfonylureas, such as glyburide, glimepiride, glipyride, glipizide, chlorpropamide and gliclazide and the glucosidase inhibitors acarbose or miglitol or insulin may be employed in formulations as described above and in amounts and dosing as indicated in the Physician's Desk Reference.

Where present, metformin or salt thereof may be employed in amounts within the range from about 500 to about 2000 mg per day which may be administered in single or divided doses one to four times daily.

Where present, the thiazolidinedione anti-diabetic agent may be employed in amounts within the range from about 0.01 to about 2000 mg/day which may be administered in single or divided doses one to four times per day.

Where present insulin may be employed in formulations, amounts and dosing as indicated by the Physician's Desk Reference.

Where present GLP-1 peptides may be administered in oral buccal formulations, by nasal administration or parenterally as described in U.S. Pat. No. 5,346,701 (Thera Tech), U.S. Pat. Nos. 5,614,492 and 5,631,224 which are incorporated herein by reference.

The antidiabetic agent may also be a PPAR a/g dual agonist such as disclosed by Murakami et al, "A Novel Insulin Sensitizer Acts As a Coligand for Peroxisome Proliferation—Activated Receptor Alpha (PPAR alpha) and PPAR gamma. Effect on PPAR alpha Activation on Abnormal Lipid Metabolism in Liver of Zucker Fatty Rats", Diabetes 47, 1841–1847 (1998).

The antidiabetic agent may be an aP2 inhibitor such as disclosed in U.S. application Ser. No. 09/391,053, filed Sep. 7, 1999, and U.S. provisional application No. 60/127,745, filed Apr. 5, 1999, employing dosages as set out herein.

The antidiabetic agent may be an SGLT2 inhibitor such as disclosed in U.S. provisional application 60/158,773 filed Oct. 12, 1999.

The compounds of formula I will be employed in a weight ratio to the PPAR a agonist, PPAR g agonist, PPAR g/a dual agonists, SGLT2 inhibitor and/or aP2 inhibitor within the range from about 0.01:1 to about 100:1, preferably from about 0.5:1 to about 5:1.

The dose administered must be carefully adjusted according to age, weight and condition of the patient, as well as the route of administration, dosage form and regimen and the desired result.

The dosages and formulations for the hypolipidemic agent and antidiabetic agent will be as disclosed in the various patents and applications discussed above and in the PDR.

The dosages and formulations for the other hypolipidemic agent, antidepressant, bone resorption inhibitor, appetite suppressant and anti-obesity agent to be employed, where applicable, will be as set out in the latest edition of the Physicians' Desk Reference.

For oral administration, a satisfactory result may be obtained employing the MTP inhibitor in an amount within the range of from about 0.01 mg/kg to about 100 mg/kg and preferably from about 0.1 mg/kg to about 75 mg/kg, one to four times daily.

A preferred oral dosage form, such as tablets or capsules, will contain the MTP inhibitor in an amount of from about 1 to about 500 mg, preferably from about 2 to about 400 mg, and more preferably from about 5 to about 250 mg, one to four times daily.

For parenteral administration, the MTP inhibitor will be employed in an amount within the range of from about 0.005 mg/kg to about 10 mg/kg and preferably from about 0.005 mg/kg to about 8 mg/kg, one to four times daily.

For oral administration, a satisfactory result may be obtained employing an HMG CoA reductase inhibitor, for example, pravastatin, lovastatin, simvastatin, atorvastatin, fluvastatin or cerivastatin in dosages employed as indicated in the Physician's Desk Reference, such as in an amount within the range of from about 1 to 2000 mg, and preferably from about 4 to about 200 mg.

The squalene synthetase inhibitor may be employed in dosages in an amount within the range of from about 10 mg to about 2000 mg and preferably from about 25 mg to about 200 mg.

A preferred oral dosage form, such as tablets or capsules, will contain the HMG CoA reductase inhibitor in an amount from about 0.1 to about 100 mg, preferably from about 5 to about 80 mg, and more preferably from about 10 to about 40 mg.

A preferred oral dosage form, such as tablets or capsules will contain the squalene synthetase inhibitor in an amount of from about 10 to about 500 mg, preferably from about 25 to about 200 mg.

The compounds of formula I and the hypolipidemic agent, antidepressant or bone resorption inhibitor may be employed together in the same oral dosage form or in separate oral dosage forms taken at the same time.

The compositions described above may be administered in the dosage forms as described above in single or divided doses of one to four times daily. It may be advisable to start a patient on a low dose combination and work up gradually to a high dose combination.

The preferred hypolipidemic agent is pravastatin, simvastatin, lovastatin, atorvastatin, fluvastatin or cerivastatin.

The compounds of the invention can be administered orally or parenterally such as subcutaneously or intravenously, as well as by nasal application, rectally or sublingually to various mammalian species known to be subject to such maladies, e.g., humans, cats, dogs and the like in an effective amount within the dosage range of about 0.1 to about 100 mg/kg, preferably about 0.2 to about 50 mg/kg and more preferably about 0.5 to about 25 mg/kg (or from about 1 to about 2500 mg, preferably from about 5 to about 2000 mg) on a regimen in single or 2 to 4 divided daily doses.

The active substance can be utilized in a composition such as tablet, capsule, ointment, hydrophilic ointment, cream, lotion, solution or suspension or in other type carrier materials such as transdermal devices, iontophoretic devices, rectal suppositories, inhalant devices and the like. The composition or carrier will contain about 5 to about 500 mg per unit of dosage of a compound of formula I. They may be compounded conventional matter with a physiologically acceptable vehicle or carrier, excipient, binder, preservative, stabilizer, flavor, etc., as called for by accepted pharmaceutical practice.

The following Examples represent preferred embodiments of the present invention. However, they should not be construed as limiting the invention in any way. The $^1$H NMR spectra were consistent with the assigned structures. MS results was obtained on a Perkin Elmer API 150Ex spectrometer, using electrospray.

EXAMPLE 1

3,5-Dichloro-4-(3-bromo-4-isobutyramidophenoxy) phenylacetic acid (a) A mechanically stirred solution of 2,6-dichlorophenol (100 g) in acetonitrile (400 mL) was cooled to 0° C. and bromine (108 g) in acetonitrile (100 mL) was added dropwise. The red solution was stirred at 0° C. for an additional two hours and an saturated aqueous solution of sodium sulphite was added until the red color disappeared. The phases were separated and the aqueous phase was extracted three times with ethyl acetate. Concentration of the combined organic phases gave 4-bromo-2,6-dichlorophenol as a yellow oil, which crystallized on standing. The crystalline material was washed with water and dried to give 126 g (85%) of colorless crystals.

(b) A mechanically stirred solution of 4-bromo-2,6-dichlorophenol (110 g), 4-fluoronitrobenzene (64 g), potassium carbonate (84 g) and copper powder (3.3 g) in dimethylform-amide (400 ml) was heated at 135° C. for 45 hours. The reaction was cooled to room temperature and concentrated. The residue was dissolved in ethyl acetate and washed twice with sodium hydroxide (2 N), twice with hydrochloric acid (1.2 N) and brine. After concentration of the organic phase, the residue was recrystallized (acetone/water, 4:1) to give 79 g (45%) of a three to one mixture of 3,5-dichloro-4-(4-nitrophenoxy)bromobenzene and 3,5-dichloro-4-(4-nitrophenoxy)benzene as yellow crystals.

(c) To the products above (40 g), dichlorobis(triphenylphosphine)palladium(II) (0.39 g) and copper(I) iodide (0.21 g) was added triethylamine (17 g) in acetonitrile (75 mL), followed by trimetylsilylacetylene (16 g) in acetonitrile (25 mL). The reaction mixture was stirred under an atmosphere of nitrogen at 60° C. for one hour and then cooled to room temperature. The reaction mixture was concentrated and the residue dissolved in ethyl acetate. The organic phase was washed twice with water and once with brine. After concentration of the organic phase, the residue was purified on column (n-heptane/ethyl acetate, 8:1) to give 42 g (53%) of 3,5-dichloro-4-(4-nitrophenoxy)trimetylsilylacetylene-benzene as yellow crystals.

(d) Cyclohexene (39 g, 0.48 mol) was added dropwise to a solution of borane (240 mL, 1 N in tetrahydrofuran) at 0° C. 3,5-Dichloro-4-(4-nitrophenoxy)trimetylsilylacetylene-benzene (26 g) in tetrahydrofuran (400 mL) was added dropwise at 0° C. and the reaction mixture was stirred at this temperature for two hours. A mixture of sodium hyroxide (170 mL, 1 N) and methanol (200 mL) was added dropwise at 0° C. followed by dropwise addition of hydrogenperoxide (90 mL, 27% w/w) at the same temperature. The mixture was stirred at 0° C. for an additional hour and concentrated. The remaining aqueous solution was acidified with hydrochloric acid (1.2 N) and extracted with three times ethyl acetate. Concentration of the organic phase gave a dark oil which was used in the next step without further purification.

(e) The crude product above was dissolved in methanol (300 mL) and thionyl chloride (8.1 g) was carefully added. The mixture was stirred at reflux for two hours. The reaction mixture was concentrated, water was added and extracted three times with ethyl acetate. Purification on column (silica, n-heptane/ethyl acetate, 4:1) gave 15 g of methyl[3,5-dichloro-4-(4-nitrophenoxy)phenyl] acetate.

(f) To a solution of methyl[3,5-dichloro-4-(4-nitrophenoxy)phenyl] acetate (14 g) in ethyl acetate (90 mL) was added platinum(IV) oxide monohydrate (0.48 g) and the mixture was stirred vigorously under hydrogen gas (1 atmospheres) for 6 hours. The suspension was filtered and the filtrate concentrated. The residue was purified on column (silica gel, n-heptane/ethyl acetate, 1:1) to give 7.0 g of methyl[3,5-dichloro-4-(4-aminophenoxy)-phenyl] acetate as orange crystals.

(g) A solution of methyl[3,5-dichloro-4-(4-nitrophenoxy)phenyl]acetate (6.5 g) in dichloromethane (250 mL) was cooled to −30° C. and 2,4,4,6-tetrabromo-2,5-cyclohexadienone (8.2 g) in dichloromethane (200 mL) was added dropwise. The reaction was stirred at −30° C. for 10 minutes and sodium hydroxide (500 mL, 1 N) was added. The phases were separated and the aqueous phase extracted three times with dichloromethane. Concentration of the organic phase and purification of the residue on column (silica gel, n-heptane/ethyl acetate, 4:1) gave 4.6 g (57%) of methyl[3,5-dichloro-4-(4-amino-3-bromophenoxy)phenyl] acetate as white crystals.

(h) To methyl[3,5-dichloro-4-(3-bromo-4-aminophenoxy)phenyl]acetate (80 mg), triethylamine (20 mg) and dichloromethane (5 mL) was added isobutyryl chloride (30 mg). After one hour, the reaction mixture was concentrated, and the residue partioned between ethyl acetate and water. The organic phase was washed with hydrochloric acid (1 N), a saturated aqueous solution of sodium hydrogencarbonate and brine. After concentration, the residue was recrystallised from a mixture of diethylether and petrolium ether, to give 40 mg (40%) of methyl[3,5-dichloro-4-(3-bromo-4-isobutyramidophenoxy)phenyl] acetate.

(i) Methyl[3,5-dichloro-4-(3-bromo-4-isobutyramidophenoxy)phenyl] acetate (25 mg), sodium hydroxide (1 N, 0.5 mL) and methanol (5 mL) was stirred at room temperature over night. After concentration, the residue was partioned between a mixture of ethylacetate and hydrochloric acid (1 N). The organic phase was concentrated and the residue recrystallised from a mixture of diethylether and petrolium ether, to give 20 mg (82%) of 3,5-dichloro-4-(3-bromo-4-isobutyramidophenoxy)phenylacetic acid.

EXAMPLE 2

3,5-Dichloro-4-(4-isobutyramidophenoxy)phenylacetic acid

Methyl[3,5-dichloro-4-(4-aminophenoxy)phenyl] acetate (33 mg, 0.10 mmol), was coupled with isobutyryl chloride (11 mg), using the method described in Example 1(h). After purification on column (silica gel, ethyl acetate/petrolium ether), 35 mg (95%) of methyl-[3,5-dichloro-4-(4-isobutyramidophenoxy)phenyl] acetate was obtained, which was hydrolysed using the method described in Example 1(i). This gave 30 mg (89%) of 3,5-dichloro-4-(4-isobutyramidophenoxy)phenylacetic acid.

EXAMPLE 3

3,5-Dichloro-4-(4-isobutyramido-3-phenylphenoxy)phenylacetic acid

Methyl[3,5-dichloro-4-(3-bromo-4-isobutyramidophenoxy)phenyl] acetate (100 mg), dichloro(1,2-bis(diphenylphosphino)butane)palladium(II) (10%), copper(II) oxide (16 mg), n-tributylphenyltin (110 mg) and dimethylformamide (3 mL) was stirred at 110° C. for 4 hours. After concentration, the residue was partioned between ethylacetate and hydrochloric acid (2 N), the organic phase washed with brine and concentrated. After purification on column (silica gel, ethyl acetate/petrolium ether, 1:2), 70 mg (70%) of methyl[3,5-dichloro-4-(4-isobutyramide-3-phenylphenoxy)-phenyl] acetate was obtained, which was hydrolyzed using the method described in Example 1(i). This gave quantiative yield of 3,5-dichloro-4-(4-isobutyramido-3-phenylphenoxy)phenylacetic acid, m/z 458.

EXAMPLE 4

3,5-Dichloro-4-(3-bromo-4-[3-methylcrotonylamido]phenoxy)phenylacetic acid

Methyl(3,5-dichloro-4-[4-amino-3-bromophenoxy]phenyl) acetate (100 mg), was coupled with crotonyl chloride (35 mg), using the method described in Example 1(h). After purification on column (silica gel, ethyl acetate/petrolium ether, 1:2), 60 mg (47%) of methyl(3,5-dichloro-4-[3-bromo-4-(3-methylcrotonoylamido)phenoxy]phenyl) acetate was obtained. A part of the obtained ester (19 mg) was hydrolysed using the method described in Example 1(i), to give 15 mg (82%) of 3,5-dichloro-4-(3-bromo-4-[3-methylcrotonylamido]-phenoxy)phenylacetic acid.

EXAMPLE 5

3,5-Dichloro-4-(3-isopropylidene-1,3-dihydro-2-oxy-5-indoloxy)phenylacetic acid

Methyl(3,5-dichloro-4-[3-bromo-4-(3-methylcrotonoylamido)phenoxy]phenyl) acetate (60 mg, 0.15 mmol), palladium(II) acetate (6 mg), triphenylphosphine (13 mg), triethylamine (30 mg) and dimethylformamide was stirred at 100° C. over night. After purification on column (silica gel, ethyl acetate/petrolium ether, 3:7), 30 mg (49%) of methyl [3,5-dichloro-4-(3-isopropylidene-1,3-dihydro-2-oxy-5-indoloxy)phenyl] acetate was obtained, which was hydrolyzed using the method described in Example 1(i). This gave 29 mg (100%) of 3,5-dichloro-4-(3-isopropylidene-1,3-dihydro-2-oxy-5-indoloxy)phenylacetic acid, m/z 392.

EXAMPLE 6

3,5-Dichloro-4-(3-isopropyl-1,3-dihydro-2-oxy-5-indoloxy)phenylacetic acid 3,5-Dichloro-4-(3-isopropylidene-1,3-dihydro-2-oxy-5-indoloxy)phenylacetic acid (20 mg), platinum(II) oxide (2 mg), ethylacetate (3 mL) and hydrogen gas (1 atmosphere) was stirred at room temperature over night. After filtration and concentration, the residue was purified on HPLC (as described for Examples 33–90) to give 6 mg (30%) of 3,5-dichloro-4-(3-isopropyl-1,3-dihydro-2-oxy-5-indoloxy) phenylacetic acid, m/z 394.

EXAMPLE 7

3,5-Dichloro-4-(4-acetamido-3-bromophenoxy)phenylacetic acid

Methyl(3,5-dichloro-4-[4-amino-3-bromophenoxy]phenyl) acetate (110 mg) was coupled with acetyl chloride (30 mg), using the method described in Example 1(h). After purification on column (silica gel, ethyl acetate/petroleum ether), 110 mg (100%) of methyl [3,5-dichloro-4-(4-acetamido-3-bromophenoxy)phenyl] acetate was obtained. A part of the obtained ester (30 mg) was hydrolysed using the method described in Example 1(i), to give 26 mg (90%) of 3,5-dichloro-4-(4-acetamido-3-bromophenoxy)phenylacetic acid, m/z 462.

EXAMPLE 8

3,5-Dichloro-4-(4-acetamido-3-phenylphenoxy)phenylacetic acid

Methyl[3,5-dichloro-4-(4-acetamido-3-bromophenoxy) phenyl] acetate (100 mg) was coupled with n-tributylphenyltin (140 mg, 0.38 mmol), using the same procedure as described in Example 3(a). This gave 70 mg (70%) of methyl(3,5-dichloro-4-[4-acetamido-3-phenylphenoxy]phenyl) acetate. A part of the obtained ester (50 mg) was hydrolysed using the method described in Example 1(i), to give 45 mg (95%) of 3,5-dichloro-4-(4-acetamido-3-phenylphenoxy)phenylacetic acid, m/z 430.

EXAMPLE 9

N-[3,5-dichloro-4-(4-isobutyramidophenoxy)phenylacetyl]glycine

A solution of 3,5-dichloro-4-(4-isobutyramidophenoxy) phenylacetic acid (70 mg), 3-ethyl-1-[3-(dimethylamino) propyl]carbodiimide hydrochloride (49 mg), 1-hydroxy-benzo-triazole hydrate, (45 mg) in dimethyl formamide (2 mL) was stirred at room temperature for 0.5 hours followed by addition of a solution of methyl glycine hydrochloride (46 mg) and triethylamine (56 mg) in dimethylformamide (1 mL). After stirring for one day, the reaction mixture was concentrated. The residue was purified by HPLC as described for Examples 33–90, to give methyl N-[3,5-dichloro-4-(4-isobutyramidophenoxy)phenylacetyl]glycine. The ester was hydrolyzed using the method described in Example 1(i) and purified as above, to give 25 mg (31%) of N-[3,5-dichloro-4-(4-isobutyramidophenoxy)phenylacetyl] glycine, m/z 439.

EXAMPLE 10

L-N-[3,5-dichloro-4-(4-isobutyramidophenoxy)phenylacetyl]alanine 3,5-Dichloro-4-(4-isobutyramidophenoxy)phenylacetic acid (70 mg) was coupled with L-methyl alanine hydrochloride (50 mg) using the method described in Example 9. This gave methyl L-N-[3,5-dichloro-4-(4-isobutyramidophenoxy)phenylacetyl]alanine, which was hydrolyzed using the method described in Example 1(i) and purified as in Example 9, to give 38 mg (45%) of L-N-[3,5-dichloro-4-(4-isobutyramidophenoxy)phenylacetyl]alanine, m/z 453.

EXAMPLE 11

L-N-[3,5-dichloro-4-(4-isobutyramidophenoxy)phenylacetyl]valine 3,5-Dichloro-4-(4-isobutyramidophenoxy)phenylacetic acid (70 mg) was coupled with L-methyl valine hydrochloride (60 mg) using the method described in Example 9. This gave methyl-L-N-[3,5-dichloro-4-(4-isobutyramidophenoxy)phenylacetyl]valine, which was hydrolyzed using the method described in Example 1(i) and purified as in Example 9, to give 50 mg (57%) of L-N-[3,5-dichloro-4-(4-isobutyramidophenoxy)phenylacetyl]valine, m/z 481.

EXAMPLE 12

N-[3,5-dichloro-4-(3-bromo-4-isobutyramidophenoxy)phenylacetyl]glycine 3,5-Dichloro-4-(3-bromo-4-isobutyramidophenoxy)phenylacetic acid (56 mg) was coupled with methyl glycine hydrochloride (31 mg) using the method described in Example 9. This gave methyl N-[3,5-dichloro-4-(3-bromo-4-isobutyramidophenoxy)phenylacetyl]-glycine, which was hydrolyzed using the method described in Example 1(i) and purified as in Example 9, to give 14 mg (22%) of N-[3,5-dichloro-4-(3-bromo-4-isobutyramidophenoxy)phenylacetyl]glycine, m/z 518.

EXAMPLE 13

L-Methyl-N-[3,5-dichloro-4-(3-bromo-4-isobutyramidophenoxy)phenylacetyl]alanine 3,5-Dichloro-4-(3-bromo-4-isobutyramidophenoxy)phenylacetic acid (83 mg) was coupled with L-methyl alanine hydrochloride (50 mg) using the method described in Example 9. This gave 45 mg (46%) of L-methyl-N-[3,5-dichloro-4-(3-bromo-4-isobutyramido-phenoxy)phenylacetyl]alanine, m/z 546.

EXAMPLE 14

L-N-[3,5-Dichloro-4-(3-bromo-4-isobutyramidophenoxy)phenylacetyl]valine 3,5-Dichloro-4-(3-bromo-4-isobutyramidophenoxy)phenylacetic acid (56 mg) was coupled with L-methyl valine hydrochloride (41 mg) using the method described in Example 9. This gave methyl L-N-[3,5-dichloro-4-(3-bromo-4-isobutyramidophenoxy)phenylacetyl]-valine, which was hydrolyzed using the method described in Example 1(i) and purified as in Example 9, to give 31 mg (50%) of L-N-[3,5-dichloro-4-(3-bromo-4-isobutyramidophenoxy)phenylacetyl]valine, m/z 560.

EXAMPLE 15

3,5-Dichloro-4-(4-isobutyramido-3-methylphenoxy)phenylacetic acid

Methyl[3,5-dichloro-4-(3-bromo-4-isobutyramidophenoxy)phenyl] acetate (100 mg) was reacted with tetramethyltin (40 mg), dichloro(1,2-bis(diphenylphosphino)butane)palladium(II), copper(II) oxide (16 mg) and dimethylformamide (3 mL) using the method described in Example 3. This gave 20 mg (23%) of methyl(3,5-dichloro-4-[4-isobutyr-amido-3-methylphenoxy]phenyl) acetate, which was hydrolyzed using the method described in Example 1(i), to give 17 mg (88%) of 3,5-dichloro-4-(4-isobutyramido-3-methyl-phenoxy)phenylacetic acid, m/z 396.

EXAMPLE 16

3,5-Dichloro-4-(3-bromo-4-trifluoroacetamidophenoxy)phenylacetic acid

Methyl[3,5-dichloro-4-(4-aminophenoxy)phenyl] acetate (60 mg) was reacted with trifluoroacetic acid anhydride (42 mg), using the method described in Example 1(h). After purification on column (silica gel, ethyl acetate/petroliium ether, 1:9), 70 mg (93%) of methyl(3,5-dichloro-4-[3-bromo-4-trifluoroacetamidophenoxy]phenyl) acetate was obtained, which was hydrolysed using the method described in Example 1(i). This gave 50 mg (73%) of 3,5-dichloro-4-(3-bromo-4-trifluoroacetamidophenoxy)phenylacetic acid.

EXAMPLE 17

3,5-Dichloro-4-(3-bromo-4-[2-chloropropionamido]phenoxy)phenylacetic acid

Methyl[3,5-dichloro-4-(4-aminophenoxy)phenyl] acetate (80 mg) was reacted with 2-chloropropionyl chloride (30 mg), using the method described in Example 1(h). After purification on column (silica gel, ethyl acetate/petrolium ether, 1:9), 80 mg (81%) of methyl (3,5-dichloro-4-[3-bromo-4-(2-chloropropionamido)phenoxy]phenyl) acetate was obtained. A part of the obtained ester (40 mg) was hydrolysed using the method described in Example 1(i), to give 25 mg (64%) of 3,5-dichloro-4-(3-bromo-4-[2-chloropropionamido]phenoxy)-phenylacetic acid.

EXAMPLE 18

3,5-Dichloro-4-(3-bromo-4-p-fluorobenzamidophenoxy)phenylacetic acid

Methyl[3,5-dichloro-4-(4-aminophenoxy)phenyl] acetate (60 mg) was coupled with p-fluorobenzoyl chloride (30 mg), using the method described in Example 1(h). After purification on column (silica gel, ethyl acetate/petrolium ether, 1:9), 80 mg (100%) of methyl(3,5-dichloro-4-[3-bromo-4-p-fluorobenzamido-phenoxy]phenyl) acetate was obtained, which was hydrolysed using the method described in Example 1(i). This gave 50 mg (65%) of 3,5-dichloro-4-(3-bromo-4-p-fluorobenzamidophenoxy)phenylacetic acid.

EXAMPLE 19

3,5-Dichloro-4-(4-isobutyramido-3-trifluoromethylphenoxy)phenylacetic acid (a) A mixture of 4-bromo-2,6-dichlorophenol (2.4 g), 5-fluoro-2-nitro-trifluoromethylbenzene (2.0 g), potassium carbonate (2.7 g) in dimethylformamide (30 mL) was heated at reflux for 2 hours. The reaction was cooled to room temperature and concentrated. The residue was partioned between ethyl acetate and hydrochloric acid (2 N), the organic phase concentrated and the residue purified on column (silica gel, ethyl acetate/petrolium ether, 5:95), to give 2.7 g of 3,5-dichloro-4-(4-nitro-3-trifluoromethylphenoxy)bromo-benzene.

(b) 3,5-Dichloro-4-(4-nitro-3-trifluoromethylphenoxy)bromobenzene (0.83 g, 2 mmol), dichlorobis(triphenylphosphine)palladium(II) (0.070 g), copper(I) iodide (20 mg), triethylamine (1.6 g), dimethylformamide (10 mL) and trimetylsilylphenyl-acetylene (0.30 g) was stirred under an atmosphere of nitrogen at 80° C. for two hours. After cooling down to room temperature, the reaction mixture was concentrated and purified on column (silica gel, ethyl acetate/petrolium ether, 5:95), to give 0.70 g of 3,5-dichloro-4-(4-nitro-3-trifluoro-methylphenoxy)trimetylsilylacetylenebenzene.

(c) 3,5-Dichloro-4-(4-nitro-3-trifluoromethylphenoxy)trimetylsilylacetylene-benzene (0.70 g) was deprotected and oxidized, using the same procedure as in Example 1(d). This gave 0.40 g of methyl[3,5-dichloro-4-(4-nitro-3-trifluoromethyl-phenoxy)phenyl] acetate.

(d) Methyl [3,5-dichloro-4-(4-nitro-3-trifluoromethylphenoxy)phenyl] acetate (0.40 g) was reduced with platinium (II)oxide, using the same procedure as in Example 1(f). This gave 0.32 g of methyl[3,5-dichloro-4-(4-amino-3-trifluoromethylphenoxy)phenyl] acetate.

(e) Methyl[3,5-dichloro-4-(4-amino-3-trifluoromethylphenoxy)phenyl] acetate (70 mg) was coupled with isobutyryl chloride (30 mg), using the method described in Example 1(h). After purification on column (silica gel, ethyl acetate/petrolium ether, 1:9), 70 mg (84%) of methyl(3,5-dichloro-4-[4-isobutyramido-3-trifluoromethylphenoxy]phenyl) acetate was obtained, which was hydrolysed using the method described in Example 1(i). This gave 50 mg (74%) of 3,5-dichloro-4-(4-isobutyramido-3-trifluoromethylphenoxy)phenylacetic acid, m/z 450.

EXAMPLE 20

3,5-Dichloro-4-(3-chloro-4-isobutyramidophenoxy)phenylacetic acid (a) Calcium hypochlorite (14 mg) was dissolved in a mixture of water (2 mL) and glacial acetic acid (one drop). Methyl[3,5-dichloro-4-(4-aminophenoxy)phenyl] acetate (35 mg) dissolved in acetone (2 mL) was added at −10° C. After stirring at −15° C. for 2 hours, the reaction mixture was concentrated and the residue partioned between sodium hydroxide (1 N) and ethyl acetate. After purification on column (silica gel, ethyl acetate/petrolium ether, 1:4), 17 mg (43%) of methyl[3,5-dichloro-4-(4-amino-3-chlorophenoxy)phenyl] acetate was obtained.

(b) Methyl[3,5-dichloro-4-(4-amino-3-chlorophenoxy)phenyl] acetate (17 mg) was coupled with isobutyryl chloride (5.0 mg), using the method described in Example 1(h). After purification on column (silica gel, ethyl acetate/petrolium ether, 1:4), 15 mg (74%) of methyl(3,5-dichloro-4-[3-chloro-4-isobutyramidophenoxy]phenyl) acetate was obtained, which was hydrolysed using the method described in Example 1(i). This gave 4 mg (27%) of 3,5-dichloro-4-(4-isobutyramido-3-trifluoromethylphenoxy)phenylacetic acid, m/z 416, 418.

EXAMPLE 21

3,5-Dichloro-4-(1,3-dihydro-2-oxy-5-imidazoloxy) phenylacetic acid (a) Nitric acid (0.5 mL) was added drop-wise at 0° C. to a stirred mixture of 3,5-dichloro-4-(4-isobutyramidophenoxy)phenylacetic acid (100 mg) and glacial acetic acid (2 mL). After stirring for 0.5 hours, the reaction mixture was partioned beetween a saturated aqueous solution of sodium hydrogencarbonate and ethyl acetate. The organic phase was washed with brine and concentrated. This gave 110 mg of methyl [3,5-dichloro-4-(4-isobutyr-amido-3-nitrophenoxy) phenyl]acetate which was used in the next step without further purification.

(b) Methyl[3,5-dichloro-4-(4-isobutyramido-3-nitrophenoxy)phenyl]acetate (45 mg) was hydrolyzed using the method described in Example 1(i), to give 30 mg (%) of 3,5-dichloro-4-(4-amino-3-nitrophenoxy)phenylacetic acid.

(c) 3,5-Dichloro-4-(4-amino-3-nitrophenoxy)phenylacetic acid (50 mg), methanol (20 mL) and thionyl chloride (2 drops) was heated at reflux for two hours. After cooling down to room temperature, the reaction mixture was partioned between an aqueous solution of sodium hydrogencarbonate (saturated) and ethyl acetate. The organic phase was washed with brine and concentrated. This gave 45 mg of methyl(3,5-dichloro-4-(4-amino-3-nitro-phenoxy)phenyl) acetate which was reduced using the method described in Example 1(f), to give 40 mg of methyl(3,5-dichloro-4-(3,4-diaminophenoxy)phenyl) acetate.

(d) Methyl(3,5-dichloro-4-(3,4-diaminophenoxy)phenyl) acetate (30 mg), N,N'-disuccinimidyl carbonate (15 mg) and acetonitrile (5 mL) was stirred at room temperature for 16 hours. After concentration, the residue was partioned between ethyl acetate and hydrochloric acid (1 N). The organic phase was washed with an aqueous solution of sodium bicarbonate (saturated) followed by brine. After purification on column (silica gel, ethyl acetate/petrolium ether, 1:2), 25 mg (77%) of methyl(3,5-dichloro-4-[1,3-dihydro-2-oxy-5-imidazoloxy]phenyl) acetate was obtained, which was hydrolyzed using the method described in example 1(i). This gave 15 mg (62%) of 3,5-dichloro-4-(1, 3-dihydro-2-oxy-5-imidazol-oxy)phenylacetic acid.

EXAMPLE 22

3,5-Dichloro-4-(3-bromo-4-isobutyramidophenoxy) phenylcinnamic acid (a) A mixture of 3,5-dichloro-4-(4-nitrophenoxy)bromobenzene and 3,5-dichloro-4-(4-nitrophenoxy)benzene (3.6 g, 3:1), ethyl acrylate (1.2 g), palladium acetate (23 mg), triphenylphosphine (50 mg), triethylamine (2.2 g) and dimethyl-formamide (30 mL) was stirred at 100° C. for 16 hours. After filtration and concentration, the residue was purified on column (silica gel, t-butyl methyl ether/petrolium ether, 5:95) to give 0.65 g (17%) of ethyl(3,5-dichloro-4-[3-bromo-4-isobutyramidophenoxy]phenyl) cinnamate.

(b) A mixture of ethyl(3,5-dichloro-4-[4-nitrophenoxy] phenyl) cinnamate (0.65 g), tindichloride dihydrate (1.0 g), ethylacetate (25 mL) and ethanol (25 mL) was heated at reflux for one hour. The reaction mixture was concentrated and the residue partioned beetween diethyl ether and sodium hydroxide (1 N). After purification on column (silica gel, ethyl acetate/petrolium ether, 3:7), 0.52 g of ethyl(3,5-dichloro-4-[4-aminophenoxy]phenyl) cinnamate was obtained.

(c) Ethyl(3,5-dichloro-4-[4-aminophenoxy]phenyl) cinnamate (0.20 g) was brominated, using the method described in Example 1(g). This gave 0.15 g of ethyl (3,5-dichloro-4-[4-amino-3-bromophenoxy]phenyl) cinnamate.

(d) Ethyl(3,5-dichloro-4-[4-amino-3-bromophenoxy]phenyl) cinnamate (70 mg) was coupled with isobutyryl chloride (30 mg), using the method described in Example 1(h). After purification on column (silica gel, ethyl acetate/petrolium ether, 1:9), 70 mg of ethyl(3,5-dichloro-4-[3-bromo-4-isobutyramidophenoxy]phenyl) acetate was obtained, which was hydrolysed using the method described in Example 1(i). This gave 50 mg of 3,5-dichloro-4-(3-bromo-4-isobutyramidophenoxy)phenylacetic acid.

EXAMPLE 23

3,5-Dichloro-4-(3-bromo-4-[2-chloropropionamido] phenoxy)phenylcinnamic acid

Ethyl(3,5-dichloro-4-[4-amino-3-bromophenoxy]phenyl) cinnamate (70 mg) was coupled with 2-chloropropionyl chloride (30 mg), using the method described in Example 1(h). After purification on column (silica gel, ethyl acetate/petrolium ether, 1:9), 45 mg (83%) of ethyl(3,5-dichloro-4-[3-bromo-4-(2-chloropropionamido)phenoxy]phenyl) cinnamate was obtained. A part of the ethyl ester (50 mg) was hydrolysed using the method described in Example 1(i), to give 40 mg (84%) of 3,5-dichloro-4-(3-bromo-4-[2-chloropropionamido]-phenoxy)phenylcinnamic acid.

EXAMPLE 24

3,5-Dichloro-4-(3-bromo-4-isobutyramidophenoxy) phenylpropionic acid (a) Ethyl(3,5-dichloro-4-[4-nitrophenoxy]phenyl) cinnamate (0.40 g) was reduced using the method described in Example 1(f), to give 0.34 g of ethyl(3,5-dichloro-4-[4-aminophenoxy]phenyl) propionate and 50 mg of ethyl(3,5-dichloro-4-[4-nitrophenoxy]phenyl) propionate as products.

(b) Ethyl(3,5-dichloro-4-[4-aminophenoxy]phenyl) propionate (0.50 g) was brominated, using the method described in Example 1(g). This gave 0.30 g of ethyl(3,5-dichloro-4-[4-amino-3-bromophenoxy]phenyl) propionate.

(c) Ethyl(3,5-dichloro-4-[4-amino-3-bromophenoxy]phenyl) propionate (50 mg) was coupled with isobutyryl chloride (30 mg), using the method described in Example 1(h). After purification on column (silica gel, ethyl acetate/petrolium ether, 1:9), 50 mg of ethyl(3,5-dichloro-4-[3-bromo-4-isobutyramidophenoxy]phenyl) propionate was obtained, which was hydrolysed using the method described in Example 1(i). This gave 40 mg of 3,5-dichloro-4-(3-bromo-4-isobutyramidophenoxy)phenylpropionic acid.

EXAMPLE 25

3,5-Dichloro-4-(3-bromo-4-p-fluorobenzamidophenoxy)phenylpropionic acid

Ethyl(3,5-dichloro-4-[4-amino-3-bromophenoxy]phenyl) propionate (70 mg) was coupled with p-fluorobenzoyl chloride (35 mg), using the method described in Example 1(h). After recrystallization (ethyl acetate/petroleum ether), 80 mg of ethyl(3,5-dichloro-4-[3-bromo-4-p-fluorobenzamidophenoxy]phenyl) propionate was obtained, which was hydrolysed using the method described in Example 1(i). This gave 60 mg of 3,5-dichloro-4-(3-bromo-4-p-fluorobenzamidophenoxy)phenylpropionic acid.

EXAMPLE 26

3,5-Dichloro-4-(3-bromo-4-[2-chloropropionamido] phenoxy)phenylpropionic acid Ethyl(3,5-dichloro-4-[4-amino-3-bromophenoxy]phenyl) propionate (80 mg) was coupled with 2-chloropropionyl chloride (30 mg), using the method described in Example 1(h). After purification on column (silica gel, ethyl acetate/petrolium ether, 1:9), 90 mg of ethyl(3,5-dichloro-4-[3-bromo-4-(2-chloropropionamido)phenoxy]phenyl) propionate was obtained, which was hydrolysed using the method described in Example 1(i). This gave 30 mg of 3,5-dichloro-4-(3-bromo-4-[2-chloropropionamido]phenoxy)phenylpropionic acid.

EXAMPLE 27

3,5-Dichloro-4-(4-isobutyramidophenoxy)phenylpropionic acid

Ethyl(3,5-dichloro-4-[4-aminophenoxy]phenyl) propionate (80 mg) was coupled with isobutyryl chloride (30 mg), using the method described in Example 1(h). After recrystallization (ethyl acetate/petrolium ether), 80 mg of ethyl(3,5-dichloro-4-[4-isobutyr-amidophenoxy]phenyl) propionate was obtained, which was hydrolysed using the method described in Example 1(i). This gave 50 mg of 3,5-dichloro-4-(4-isobutyramidophenoxy)-phenylpropionic acid, m/z 382.

EXAMPLE 28

3,5-Dichloro-4-(4-[2-chloropropionamido]phenoxy) phenylcinnamic acid

Stannic chloride (50 mg) was added to a stirred mixture of ethyl(3,5-dichloro-4-[4-aminophenoxy]phenyl) cinnamate (0.10 g), triethylamine (40 mg), dichloromethane (5 mL) and 2-chloropropionyl chloride (50 mg). The reaction mixture was heated at reflux for 16 hours. After concentration and partionating of the residue with ethyl acetate and hydrochloric acid (2 N), 80 mg of methyl(3,5-dichloro-4-[4-(2-chloropropionamido)-phenoxy]phenyl) cinnamate was obtained. The intermediate methyl ester was hydrolyzed using the method described in Example 1(i), to give 60 mg of 3,5-dichloro-4-(4-[2-chloropropionamido]phenoxy)phenylcinnamic acid.

EXAMPLE 29

3,5-Dichloro-4-(3-methyl-1,3-dihydro-2-oxy-5-indoloxy)phenylcinnamic acid (a) A stirred solution of 2,4,6-tribromophenol (3.8 g), 4-fluoronitrobenzene (1:6 g), cesium carbonate (3.7 g) in dimethylformamide (8 mL) was heated at reflux until the starting materials were consumed. The reaction was cooled to room temperature and concentrated. The residue was dissolved in ethyl acetate and washed with sodium hydroxide (2 N), hydrochloric acid (2 N) and brine. Concentration of the organic phase gave 1,3,5-tribromo-4-(4-nitrophenoxy)benzene in quantitative yield. The crude product was used directly in the next step.

(b) 1,3,5-Tribromo-4-(4-nitrophenoxy)benzene (1.0 g) was coupled with ethyl acrylate (0.45 g) using the method described in Example 22(a). After purification on column (silica gel, ethyl acetate/petroleum ether, 1:9), 0.70 g of ethyl(3,5-dibromo-4-[4-nitrophenoxy]phenyl) cinnamate was obtained.

(c) Ethyl(3,5-dibromo-4-[4-nitrophenoxy]phenyl) cinnamate (0.50 g) was reduced with tindichloride dihydrate (0.70 g), using the procedure described in Example 22(b). After purification, 0.35 g (79%) of ethyl(3,5-dibromo-4-[4-aminophenoxy]phenyl) cinnamate was obtained.

(d) 2-Chloropropionyl chloride (0.14 g) and triethylamine (0.10 g) was added at 0° C. to a solution of ethyl(3,5-dibromo-4-[4-aminophenoxy]phenyl) cinnamate (0.30 g) in dichloromethane (15 mL). After 0.5 hours, stannic chloride (2 drops) was added and the reaction mixture was stirred at room temperature for one hour. The reaction mixture was diluted with dichloromethane and washed with water and brine. After concentration of the organic phase, the residue was purified on column (silica gel, ethyl acetate/petrolium ether, 1:9), to give 0.10 g (30%) of ethyl(3,5-dibromo-4-(3-methyl-1,3-dihydro-2-oxy-5-indoloxy)phenyl) cinnamate, which was hydrolysed using the method described in Example 1(i). This gave 35 mg of 3,5-dibromo-4-(3-methyl-1,3-dihydro-2-oxy-5-indoloxy)phenyl-cinnamic acid.

EXAMPLE 30

3,5-Dibromo-4-(3-methyl-1,3-dihydro-2-oxy-5-indoloxy)phenoxyacetic acid (a) A stirred reaction mixture of 2,6-dibromo-4-fluorophenol (35 g), 4-fluoronitrobenzene (17.5 g), potassium carbonate (19.1 g) in dimethylformamide (70 ml) was heated at reflux for two hours. The reaction mixture was cooled to room temperature and concentrated. The residue was dissolved in ethyl acetate and washed with hydrochloric acid (1 N) and brine. After evaporation of the organic phase, the residue was treated with petrolium ether and the precipitate collected. The yield of 3,5-dibromo-4-(4-nitrophenoxy)fluorobenzene was quantitative.

(b) Sodium methylate (2.2 g) was added to a solution of 3,5-dibromo-4-(4-nitrophenoxy)fluorobenzene (10 g) and dimethylformamide (25 mL). The reaction mixture was heated at 100° C. for 15 minutes. After cooling down to room temperature, concentration and purification on column (silica gel, ethyl acetate/petrolium ether, 1:9), 5.4 g of 3,5-dibromo-4-(4-nitrophenoxy)anisole was obtained.

(c) Boronitribromide (12 mL, 1 N in dichloromethane) was added to a cooled mixture of 3,5-dibromo-4-(4-nitrophenoxy)anisole (2.0 g) in dichloromethane (50 mL) and left for 16 hours at room temperature. Hydrochloric acid (2 N)

was added and the reaction mixture was heated at reflux for 15 minutes. The reaction mixture was diluted with dichloromethane, washed with water and concentrated. Quantitative yield of 3,5-dibromo-4-(4-nitrophenoxy) phenol was obtained.

(d) 3,5-Dibromo-4-(4-nitrophenoxy)phenol (2.0 g), alpha-bromoacetate (3.4 mL), potassium carbonate (1.4 g) and acetone (50 mL) was heated at reflux for 4 hours. After cooling down to room temperature, the reaction mixture was diluted with diethylether, filtered and purified on column (silica gel, ethylacetate/petrolium ether, 1:9). This gave 2.5 g of ethyl(3,5-dibromo-4-[4-nitrophenoxy]phenoxy) acetate.

(e) Ethyl(3,5-dibromo-4-[4-nitrophenoxy]phenoxy) acetate (2.4 g), zink chloride (5.7 g), ethylacetate (30 mL) and ethanol (30 mL) was heated at reflux for two hours. After cooling down to room temperature, the reaction mixture was diluted with ethylacetate, washed with a saturated aqueous solution of sodium hydrogencarbonate and the organic phase dried over potassium carbonate. After concentration, 2.0 g of ethyl(3,5-dibromo-4-[4-aminophenoxy] phenoxy) acetate was obtained as a brown oil.

(f) Ethyl(3,5-dibromo-4-[4-aminophenoxy]phenoxy) acetate (1.0 g) was coupled with 2-chloropropionyl chloride and subsequently ring-closed, using the procedure described in Example 29(d). After purification on column (silica gel, ethyl acetate/petrolium ether, 1:4), 0.5 g of ethyl(3,5-dibromo-4-[3-methyl-1,3-dihydro-2-oxy-5-indoloxy]phenoxy) acetate was obtained. A part of the intermediate ethyl ester was hydrolyzed using the method described in Example 1(i), to give 0.14 g of 3,5-dibromo-4-(3-methyl-1,3-dihydro-2-oxy-5-indoloxy)-phenoxyacetic acid.

EXAMPLE 31

3,5-dichloro-4-(3-4-isobutyramidophenoxy)benzoyl phenylsulfonamide

A mixture of 3,5-dichloro-4-(3-bromo-4-isobutyramidophenoxy)phenylacetic acid (46 mg, 0.10 mmol), benzene sulphonamide (16.5 mg. 0.105 mmol), dimethyl aminopyridine (13 mg, 0.105 mmol), 3-ethyl-1-[3-(dimethylamino) propyl]carbodiimide hydrochloride (20 mg, 0.105 mmol), in dichloromethane (10 mL) was stirred at room temperature for 4 days. Reaction mixture was poured into an aqueous solution of hydrochloric acid (1 N). The aqueous layer was extracted with ethyl acetate, and the combined organic layer was washed with water, dried over $MgSO_4$, filtered, and concentrated at reduced pressure. The residue was purified on column (silica gel, gradient: n-heptane/ethyl acetate 1:9 to n-heptane/ethyl acetate 3:7) to give product 53 mg (88%) of 3,5-dichloro-4-(3-bromo-4-isobutyramido-phenoxy)benzoyl phenylsulfonamide, m/z 600.

EXAMPLE 32

3,5-Diisopropyl-4-(7-2H-1,4-benzoxazinoxy-3(4H)-one)phenylpropionic acid (a) 5-Fluoro-2-nitrophenol (10.3 g), potassium carbonate (27.1 g), methyl iodide (11.1 g) and acetone (100 mL) was heated at reflux until the starting materials were consumed. After cooling down to room temperature, the reaction mixture was diluted with ethylacetate, washed with hydrogen chloride (1 N) and brine. After puridication on column (silica gel, ethyl acetate/petrolium ether, 1:9), 10.8 g (96%) of of 5-fluoro-2-nitroanisole was obtained.

(b) 2,6-Diisopropylphenol (11.6 g) was coupled with 5-fluoro-2-nitroanisole (17.5 g), using the same procedure as described in Example 30(a). After purification on column (silica gel, ethyl acetate/petrolium ether, 1:9), 16.6 g (87%) of 2-nitro-5-(2,6-diisopropyl-phenoxy)anisole was obtained.

(c) Stannous chloride (0.46 mL) was carefully added under nitrogen gas to a ice-cooled mixture of 2-nitro-5-(2, 6-diisopropylphenoxy)anisole (3.8 g), chloromethyl methyl ether (1.8 mL) and dichloromethane (5 mL). After 16 hours, the reaction mixture was concentrated and purified on column (silica gel, ethyl acetate/petroliumether, 97:3), to give 1.4 g of 3,5-diisopropyl-4-(3-methoxy-4-nitrophenoxy)benzylchloride.

(d) Sodium hydride (60%, in oil) was washed with petrolium ether under nitrogen gas. Diethyl malonate (0.52 mL) was added, followed by 3,5-diisopropyl-4-(4-nitro-3-methoxyphenoxy)benzylchloride (1.0 g) in tetrahydrofuran (5 mL). After 20 hours, the reaction mixture was concentrated, diluted with ethylacetate and washed with water and brine. After purification on column (silica gel, ethyl acetate/ petrolium ether, 1:9), 1.4 g of diethyl(3,5-diisopropyl-4-[3-methoxy-4-nitrophenoxy]benzyl) malonate was obtained.

(e) Sulphuric acid (1.0 mL, 20%) was added to a mixture of diethyl(3,5-diisopropyl-4-[3-methoxy-4-nitrophenoxy] benzyl) malonate (1.4 g), acetic acid (5 mL) and water (5 mL). After heating for 8 hours at 80° C., the reaction mixture was concentrated and ethyl acetate was added to the residue. The organic phase was washed with water and brine. After recrystallization (ethyl acetate/petrolium ether), 1.1 g of 3,5-diisopropyl-4-(3-methoxy-4-nitrophenoxy)phenylpropionic acid was obtained.

(f) 3,5-Diisopropyl-4-(3-methoxy-4-nitrophenoxy)phenylpropionic acid (0.98 g) was demethylated using the same procedure as described in Example 30(c). After purification on column (dichloromethane/methanol/acetic acid, 97:3: 0.1), 0.90 g of 3,5-diisopropyl-4-(3-hydroxy-4-nitrophenoxy)phenylpropionic acid was obtained.

(g) 3,5-Diisopropyl-4-(3-hydroxy-4-nitrophenoxy)phenylpropionic acid (0.89 g), methanol (25 mL) and thionyl chloride (3 drops) was stirred at room temperature for 22 hours. The reaction mixture was diluted with ethyl acetate and washed with water and brine. After concentration, the residue was recrystallized (ethyl acetate/petrolium ether) to give 0.40 g of methyl(3,5-diisopropyl-4-[3-hydroxy-4-nitrophenoxy]phenyl) propionate.

(h) Methyl(3,5-diisopropyl-4-[3-hydroxy-4-nitrophenoxy]phenyl) propionate (0.30 g), methanol (10 mL), palladium on carbon (10%) and 1–2 atmospheres of hydrogen gas was stirred at room temperature for 4 hours. After filtration, 0.28 g of methyl(3,5-diisopropyl-4-[4-amino-3-hydroxyphenoxy]phenyl) propionate was obtained.

(i) Chloroacetyl chloride (0.035 mL) was added dropwise to an ice-cooled mixture of methyl(3,5-diisopropyl-4-[4-amino-3-hydroxyphenoxy]phenyl) propionate (0.15 g), sodium hydrogencarbonate (0.10 g) and dioxane (5 mL). The reaction mixture was stirred at room temperature for 40 minutes and water (1 mL) was added. This gave a mixture of 3,5-diisopropyl-4-(7-2H-1,4-benzoxazinoxy-3(4H)-one) phenylpropionic acid and methyl(3,5-diisopropyl-4-[7-2H-1,4-benzoxazinoxy-3(4H)-one]phenyl) propionate. The propionic acid was re-esterified by using the same procedure as described in Example 32(g). After purification of the collected methyl ester on column (ethyl acetate/petrolium ether, 4:1), 55 mg (34%) of methyl(3,5-diisopropyl-4-[7-2H-1,4-benzoxazinoxy-3(4H)-one]phenyl) propionate was obtained. The methyl ester was hydrolyzed by using the procedure described in Example 1(i).

General Procedures for the Preparation of Examples 33–80

Four different methods (A–D), were used for the preparation of the Examples. The method is indicated in the table below. All examples were hydrolysed and purified by the general procedures given below.

Method A: The appropriate carboxylic acids (3 equivalents) were placed in separate reaction vessels. To each reaction vessel was added a solution consisting of 1-hydroxybenzo-triazole hydrate (1.7 equivalents), 3-ethyl-1-[3-(dimethylamino)propyl]carbodiimide hydrochloride (1.4 equivalents) and dichloromethane (1.0 mL), and the mixture was stirred under argon at room temperature for one hour. A solution of Example 1(f) or the methyl ester of Example 2 in dichloromethane (1 mL) was added to each reaction vessel, the vessels were sealed and stirred under argon at 40° C. for 18 hours.

Method B: In analogy with Method A, but after 18 hours benzotriazole-1-yl-oxy-tris-pyrrolidino phosphonium hexafluorophosphate (1.1 equivalents) in dichloromethane (0.5 mL) was added to each vessel.

Method C: The appropriate sulfonyl chloride (3.0 equivalents were placed in separate reaction vessels. To each reaction vessel was added pyridine (1 mL) in dichloromethane (0.5 mL). A solution of Example 1(f) or the methyl ester of Example 2 in dichloromethane (1 mL) was added to each reaction vessel, the vessels were sealed and stirred under Argon at 40° C. for 18 hours.

Method D: The appropriate isocyanate (1.5 equivalents) in dichloromethane (1.0 mL) were placed in separate reaction vessels. A solution of Example 1(f) in dichloromethane (1 mL) was added to each reaction vessel, the vessels were sealed and stirred under Argon at 40° C. for 18 hours Deprotection: On completion of reaction, the solvent was concentrated, the residue dissolved in methanol (1 mL) and sodium hydroxide (6 N, 0.5 mL) was added. The reaction mixture was stirred at 40° C. for 24 hours.

Work up procedure: The reaction mixture was concentrated, the residue dissolved in a mixture of acetonitrile, methanol and water and subjected semi-prep HPLC, using gradient elution (Eluents: Solvent A: 10% acetonitrile+10 mmol formic acid, Solvent B: acetonitrile+10 mmol formic acid; Gradient: 0–1 min 90% A, 1–7 min to 100% B, 7–9 min 100% B, 9–10 min return to 10% A; Column: Zorbax-$C_8$-5μ-21.5×50, flow 25 mL/minute).

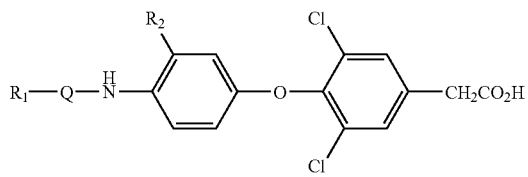

| Example | Method | $R_1$—Q— | $R_2$ | MS | Yield[1] | HPLC[2] |
|---|---|---|---|---|---|---|
| 33 | A | PhC(O)C(CH₃)— | H | 417.5 | 62 | — |
| 34 | C | PhS(O)₂— | H | 453.3 | 48 | — |
| 35 | D | PhNHC(O)C(CH₃)— | H | 432.1 | 80 | 5.46 |
| 36 | D | PhNHC(S)C(CH₃)— | H | 448.1 | 68 | 5.92 |
| 37 | A | CH₃CH₂C(O)C(CH₃)— | H | 369.2 | 18 | 4.84 |

-continued
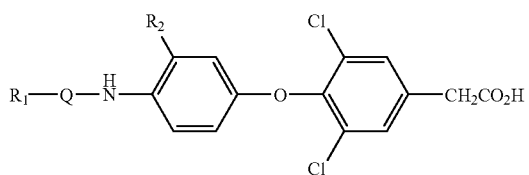
| Example | Method | R₁—Q— | R₂ | MS | Yield[1] | HPLC[2] |
|---|---|---|---|---|---|---|
| 38 | A | (propyl-C(=O)-) | H | 383.3 | 26 | 5.15 |
| 39 | A | (butyl-C(=O)-) | H | 397.1 | 40 | 5.38 |
| 40 | A | (isobutyl-C(=O)-) | H | 397.1 | 22 | 5.46 |
| 41 | A | (tert-butyl-C(=O)-) | H | 397.1 | 58 | 5.53 |
| 42 | A | (HOOC-CH=CH-C(=O)-) | H | 411.2 | 64 | 4.56 |
| 43 | A | (sec-pentyl-C(=O)-) | H | 411.2 | 53 | 5.76 |
| 44 | A | (3-ethylpropyl-C(=O)-) | H | 411.2 | 15 | 5.69 |
| 45 | A | (2-methylbutyl-C(=O)-) | H | 411.2 | 17 | 5.76 |
| 46 | A | (isopentyl-C(=O)-) | H | 411.2 | 18 | 4.84 |
| 47 | A | (neopentyl-C(=O)-) | H | 411.2 | 24 | 5.92 |

-continued
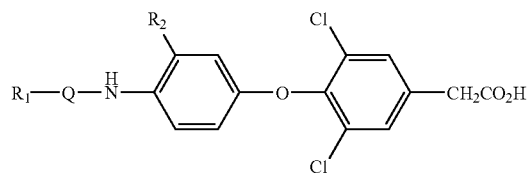
| Example | Method | R₁—Q— | R₂ | MS | Yield[1] | HPLC[2] |
|---|---|---|---|---|---|---|
| 48 | B | HOOC-(CH₂)₃-C(=O)- | H | 441.2 | 28 | 5.31 |
| 49 | A | CH₃-(CH₂)₅-C(=O)- | H | 439.4 | 23 | 6.38 |
| 50 | B | 4-(CH₃NH)-C₆H₄-C(=O)- | H | 447.1 | 33 | 5.30 |
| 51 | B | PhNH-CH₂-C(=O)- | H | 446.4 | 54 | 5.53 |
| 52 | A | CH₃-(CH₂)₈-C(=O)- | H | 467.3 | 27 | 6.69 |
| 53 | B | quinolin-8-yl-C(=O)- | H | 468.2 | 29 | 6.22 |
| 54 | A | HOOC-(CH₂)₅-C(=O)- | H | 469.4 | 45 | 4.77 |
| 55 | C | 4-MeO-C₆H₄-SO₂- | H | 483.2 | 8 | — |
| 56 | C | 5-(Me₂N)-naphthalen-1-yl-SO₂- | H | 546.2 | 21 | — |

-continued
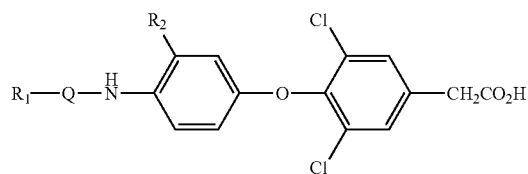
| Example | Method | R₁—Q— | R₂ | MS | Yield[1] | HPLC[2] |
|---|---|---|---|---|---|---|
| 57 | A | | Br | 448.0 | 24 | 5.69 |
| 58 | A | | Br | 475.9 | 11 | 6.07 |
| 59 | A | | Br | 490.0 | 23 | 5.53 |
| 60 | A | | Br | 490.0 | 17 | 6.30 |
| 61 | A | | Br | 490.2 | 20 | 6.30 |
| 62 | B | | Br | 600.1 | 18 | 6.53 |
| 63 | B | | Br | 543.1 | 16 | 4.69 |
| 64 | B | | H | 471.1 | 13 | 4.73 |

-continued
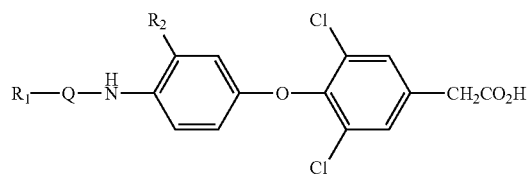
| Example | Method | R₁—Q— | R₂ | MS | Yield¹ | HPLC² |
|---|---|---|---|---|---|---|
| 65 | B | piperidine-CH₂CH₂-C(=O)-C(CH₃)- | B | 452.0 | 80 | 4.12 |
| 66 | A | cyclohexyl-C(=O)-C(CH₃)- | H | 423.2 | 30 | 6.10 |
| 67 | A | (dipropyl)CH-C(=O)-C(CH₃)- | H | 439.4 | 29 | 6.34 |
| 68 | A | (ethyl)(butyl)CH-C(=O)-C(CH₃)- | H | 439.4 | 31 | 6.34 |
| 69 | A | cyclobutyl-C(=O)-C(CH₃)- | H | 395.0 | 43 | 5.78 |
| 70 | A | cyclopentyl-C(=O)-C(CH₃)- | H | 409.1 | 20 | 6.02 |
| 71 | A | cycloheptyl-C(=O)-C(CH₃)- | H | 437.3 | 36 | 6.23 |
| 72 | A | (butyl)(methyl)CH-C(=O)-C(CH₃)- | H | 425.0 | 48 | 6.23 |

-continued

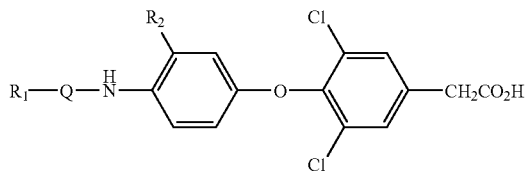

| Example | Method | R₁—Q— | R₂ | MS | Yield[1] | HPLC[2] |
|---|---|---|---|---|---|---|
| 73 | B | (1-methylindol-2-yl-carbonyl) | H | 470.3 | 42 | 6.28 |
| 74 | B | (N,N-dimethyl-phenylalanyl) | H | 488.0 | 62 | 4.39 |
| 75 | C | methylsulfonyl | H | 390.6 | 26 | 4.57 |
| 76 | C | propylsulfonyl | H | 419.9 | 24 | 4.79 |
| 77 | C | butylsulfonyl | H | 420.2 | 23 | 5.10 |
| 78 | C | octylsulfonyl | H | 489.1 | 13 | 6.13 |
| 79 | C | ethylsulfonyl | H | 404.6 | 11 | 4.40 |
| 80 | C | (E)-styrylsulfonyl | H | 479.0 | 37 | 5.33 |

[1]Yield (%) calculated from starting material.
[2]Retention times in minutes, measured by using the same eluent as described for the purification step, but with a Zorbax-$C_8$-5μ-4.6 × 50 mm, flow 3 ml/min.

EXAMPLE 81

3,5-Dichloro-4-[3-((E)-2-carboxyvinyl)-4-isobutyramidophenoxy]phenylacetic acid (a) A mixture of methyl[3,5-dichloro-4-(3-bromo-4-isobutyramidophenoxy)-phenyl] acetate (48 mg, 0.1 mmol), ethyl acrylate (50 mg, 0.5 mmol), palladium acetate (2.3 mg, 0.01 mmol), tri-o-tolyl phosphine (6.7 mg, 0.022 mmol), triethyl amine (40 mg, 0.4 mmol) in DMF (3 mL) was degassed under a nitrogen flow for 2 minutes. The reaction mixture was stirred and heated at 120° C. for 20 hours. The reaction mixture was allowed to cool down to room temperature and poured into an aqueous solution of hydrochloric acid (1N). The aqueous layer was extracted with ethyl acetate, and the combined organic layers was washed with water, dried over MgSO$_4$, filtered, and concentrated at reduced pressure. The residue was purified on column (silica gel, gradient: from n-heptane/ethyl acetate 1:9 to n-heptane/ethyl acetate 3:7) to give 16 mg of methyl{3,5-dichloro-4-[3-((E)-2-carboxyvinyl)-4-isobutyramidophenoxy]phenyl}acetate, m/z 494.

(b) Methyl{3,5-dichloro-4-[3-((E)-2-carboxyvinyl)-4-isobutyramidophenoxy]phenyl}acetate(10 mg, 0.02 mmol), LiOH (2 mL, 1N) and THF (1 mL) was stirred at room temperature for 16 hours. The reaction mixture was poured into an aqueous solution of hydrochloric acid (1N). The aqueous layer was extracted with ethyl acetate, and the combined organic layers was washed with water, dried over MgSO$_4$, filtered, and concentrated at reduced pressure to give 3.2 mg (35%) of 3,5-dichloro-4-[3-((E)-2-carboxyvinyl)-4-isobutyr-amidophenoxy]phenylacetic acid, m/z 452.

The compounds of Examples 1–81 exhibit binding affinities to the thyroid receptor beta in the range of IC$_{50}$ of 0.2 to 10000 nM.

The invention claimed is:

1. A compound of the general formula:

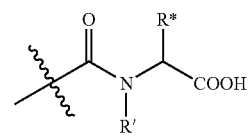

Structure I or a pharmaceutically acceptable salt thereof, wherein:

$R_1$ is selected from $C_{5-15}$ aryl; $C_{5-15}$ heteroaryl; $C_{1-20}$ alkyl; $C_{2-20}$ alkenyl; $C_{2-20}$ alkynyl; $C_{3-15}$ cycloalkyl, said alkyl, alkenyl, alkynyl, cycloalkyl, being optionally substituted with 1, 2 or 3 groups $R^a$ which groups may be the same or different, said aryl and heteroaryl being optionally substituted with 1, 2 or 3 groups $R^b$ which groups may be the same or different;

$R_2$ is selected from hydrogen; halogen; —NO$_2$; —CN; $C_{6-10}$ aryl; $C_{5-10}$ heteroaryl; $C_{1-10}$ alkyl; $C_{3-8}$ cycloalkyl; $C_{2-10}$ alkenyl; $C_{2-10}$ alkynyl, said alkyl, cycloalkyl, alkenyl, alkynyl optionally substituted with 1, 2 or 3 groups $R^a$ which groups may be the same or different said aryl, heteroaryl optionally substituted with 1, 2 or 3 groups of $R^b$ which groups may be the same or different;

$R_1$ can be linked through the available atoms to position $R_2$, thus forming an aza containing $C_5$–$C_8$ heterocyclic ring, saturated or partially unsaturated, and optionally substituted with 1, 2 or 3 groups of $R^c$ which groups may be the same or different;

Q is selected from —CO—; —SO—; —SO$_2$—; —NHCS— or —NHCO—;

$R_3$ and $R_4$ are independently selected from: halogen; $C_{1-4}$ alkyl; $C_{3-4}$ cycloalkyl; $C_{2-4}$ alkenyl; and $C_{2-4}$ alkynyl, said alkyl, cycloalkyl, alkenyl, alkynyl, or a bioisosteric equivalent thereof and optionally substituted with 1, 2 or 3 groups $R^d$ which groups may be the same or different;

Z is selected from: —(CH$_2$)$_n$—; —CH═CH—; —O(CH$_2$)$_m$—; and NH(CH$_2$)$_m$—;

n is 0, 1, 2 or 3;

m is 1 or 2;

$R_5$ is independently selected from: carboxylic acid (—CO$_2$H); phosphonic acid (—PO(OH)$_2$); phosphamic acid (—PO(OH)NH$_2$); sulphonic acid (—SO$_2$OH); hydroxamic acid (—CONHOH); oxamic acid (—NHCOCO$_2$H); malonamic acid (—NHCOCH$_2$CO$_2$H); acylsulphonamide (—CONHSO$_2$R'); and a carboxylic acid amide (—CONR'R") where R' is H or phenyl, and the amine portion of the amide is derived either from a L or D α-amino acid; or from a mixture of L and D α-aminoacid stereoisomers such that the general structure —CONR'R" can be represented by:

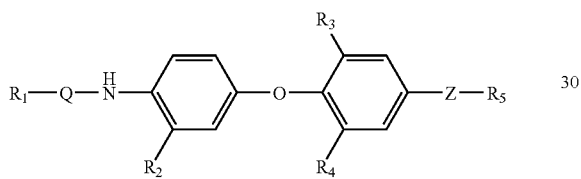

R* is any of the side chains found in the naturally occurring α-amino acids, or wherein R' and R* are connected to form 4 to 8-membered rings;

or any other possible bioisosteric equivalent of all the groups above;

$R^a$ is selected from: hydrogen; halogen; —CN; —CO$_2$H; —CHO; —NO$_2$; $C_{6-10}$ aryl; $C_{5-10}$ heteroaryl; $C_{1-4}$ alkoxy; $C_{2-4}$ alkenoxy; $C_{2-4}$ alkynoxy; $C_{6-10}$ aryloxy; $C_{5-10}$ heteroaryloxy; $C_{1-4}$ alkylthio; $C_{2-4}$ alkenylthio; $C_{2-4}$ alkynylthio; $C_{6-10}$ arylthio; $C_{5-10}$ heteroarylthio; —N(C$_{1-6}$ alkyl)$_2$; —NH(C$_{1-6}$ alkyl); —N(C$_{2-6}$ alkenyl)$_2$; —NH(C$_{2-6}$ alkenyl); —N(C$_{6-10}$ aryl)$_2$; —NH(C$_{6-10}$ aryl); —N(C$_{5-10}$ heteroaryl)$_2$; —NH(C$_{6-10}$ heteroaryl); —N(C$_{1-6}$ alkyl)(C$_{2-6}$ alkenyl); —N(C$_{1-6}$ alkyl)(C$_{6-10}$ aryl; —N(C$_{1-6}$ alkyl)(C$_{6-10}$ heteroaryl); —N(C$_{2-6}$ alkenyl)(C$_{6-10}$ aryl); —N(C$_{2-6}$ alkenyl)(C$_{5-10}$ heteroaryl); —N(C$_{6-10}$ aryl)(C$_{5-10}$ heteroaryl) or a bioisosteric equivalent thereof;

$R^b$ is selected from: hydrogen; halogen; —CN; —CO$_2$H; —CHO; —NO$_2$; —OH; $C_{1-4}$ alkyl; $C_{2-4}$ alkenyl; $C_{2-4}$ alkynyl; $C_{1-4}$ alkoxy; $C_{2-4}$ alkenoxy; $C_{2-4}$ alkynoxy; $C_{6-10}$ aryloxy; $C_{5-10}$ heteroaryloxy; $C_{1-4}$ alkylthio; $C_{2-4}$ alkenylthio; $C_{2-4}$ alkynylthio; $C_{6-10}$ arylthio; $C_{5-10}$ heteroarylthio; —N(C$_{1-6}$ alkyl)$_2$; —NH(C$_{1-6}$ alkyl); —N(C$_{2-6}$ alkenyl)$_2$; —NH(C$_{2-6}$ alkenyl); —N(C$_{6-10}$ aryl)$_2$; —NH(C$_{6-10}$ aryl); —N(C$_{5-10}$ heteroaryl)$_2$; —NH(C$_{6-10}$ heteroaryl); —N(C$_{1-6}$ alkyl)(C$_{2-6}$ alkenyl); —N(C$_{1-6}$ alkyl)(C$_{6-10}$ aryl); —N(C$_{1-6}$ alkyl)(C$_{6-10}$ heteroaryl); —N(C$_{2-6}$ alkenyl)(C$_{6-10}$ aryl); —N(C$_{2-6}$ alkenyl)(C$_{5-10}$ heteroaryl); —N(C$_{6-10}$ aryl)(C$_{5-10}$ heteroaryl) or a bioisosteric equivalent thereof;

$R^c$ is selected from: hydrogen; $C_{1-4}$ alkyl; $C_{2-4}$ alkenyl; $C_{2-4}$ alkynyl or a bioisosteric equivalent;

$R^d$ is selected from: hydrogen; halogen, or a bioisosteric equivalent.

2. The compound as defined in claim 1 wherein:

$R_1$ is selected from $C_{6-10}$ aryl, $C_{5-8}$ heteroaryl, $C_{1-10}$ alkyl, $C_{2-10}$ alkenyl or $C_{2-10}$ alkynyl or $C_{3-10}$ cycloalkyl;

$R_2$ is selected from hydrogen, halogen, $C_{6-10}$ aryl or $C_{1-4}$ alkyl;

$R_3$ and $R_4$ is selected from halogen and $C_{1-3}$ alkyl;

Z is —(CH$_2$)$_n$— or —CH═CH—;

$R_5$ is —CO$_2$H or a carboxylic acid amide —CONR'R".

3. The compound as defined in claim 1 which is:

3,5-Dichloro-4-(3-bromo-4-isobutyramidophenoxy)phenylacetic acid;
3,5-Dichloro-4-(4-isobutyramidophenoxy)phenylacetic acid;
3,5-Dichloro-4-(3-phenyl-4-isobutyramidophenoxy)phenylacetic acid;
3,5-Dichloro-4-(3-bromo-4-[3-methylcrotonylamido]phenoxy)phenylacetic acid;
3,5-Dichloro-4-(3-isopropylidene-1,3-dihydro-2-oxy-5-indoloxy)phenylacetic acid
3,5-Dichloro-4-(3-isopropyl-1,3-dihydro-2-oxy-5-indoloxy)phenylacetic acid;
3,5-Dichloro-4-(3-bromo-4-acetamidophenoxy)phenylacetic acid
3,5-Dichloro-4-(4-acetamido-3-phenylphenoxy)phenylacetic acid;
N-[3,5-dichloro-4-(4-isobutyramidophenoxy)phenylacetyl]glycine;
L-N-[3,5-dichloro-4-(4-isobutyramidophenoxy)phenylacetyl]alanine;
L-N-[3,5-dichloro-4-(4-isobutyramidophenoxy)phenylacetyl]valine;
N-[3,5-dichloro-4-(4-isobutyramido-3-bromophenoxy)phenylacetyl]glycine;
L-Methyl-N-[3,5-dichloro-4-(4-isobutyramido-3-bromophenoxy)phenylacetyl]alanine;
L-N-[3,5-Dichloro-4-(4-isobutyramido-3-bromophenoxy)phenylacetyl]valine;
3,5-Dichloro-4-(4-isobutyramido-3-methylphenoxy)phenylacetic acid;
3,5-Dichloro-4-(4-trifluoroacetamido-3-bromophenoxy)phenylacetic acid;
3,5-Dichloro-4-(4-[2-chloropropionamido]-3-bromophenoxy)phenylacetic acid;
3,5-Dichloro-4-(4-p-fluorobenzamido-3-bromophenoxy)phenylacetic acid;
3,5-Dichloro-4-(4-isobutyramido-3-trifluoromethylphenoxy)phenylacetic acid;
3,5-Dichloro-4-(3-chloro-4-isobutyramidophenoxy)phenylacetic acid;
3,5-Dichloro-4-(1,3-dihydro-2-oxy-5-imidazoloxy)phenylacetic acid;
3,5-Dichloro-4-(3-bromo-4-isobutyramidophenoxy)phenylcinnamic acid;
3,5-Dichloro-4-(3-bromo-4-[2-chloropropionamido]phenoxy)phenylcinnamic acid;
3,5-Dichloro-4-(3-bromo-4-isobutyramidophenoxy)phenylpropionic acid;
3,5-Dichloro-4-(3-bromo-4-p-fluorobenzamidophenoxy)phenylpropionic acid;
3,5-Dichloro-4-(3-bromo-4-[2-chloropropionamido]phenoxy)phenylpropionic acid;
3,5-Dichloro-4-(4-isobutyramidophenoxy)phenylpropionic acid;
3,5-Dichloro-4-(4-[2-chloropropionamido]phenoxy)phenylcinnamic acid;
3,5-Dibromo-4-(3-methyl-1,3-dihydro-2-oxy-5-indoloxy)phenylcinnamic acid;
3,5-Dibromo-4-(3-methyl-1,3-dihydro-2-oxy-5-indoloxy)phenoxyacetic acid;
3,5-Diisopropyl-4-(7-2H-1,4-benzoxazinoxy-3(4H)-one)phenylpropionic acid;
3,5-Dichloro-4-[3-((E)-2-carboxyvinyl)-4-isobutyramidophenoxy]phenylacetic acid;
3,5-Dichloro-4-(3-bromo-4-isobutyramidophenoxy)benzoyl phenylsulfonamide;

or a compound shown in the table below,

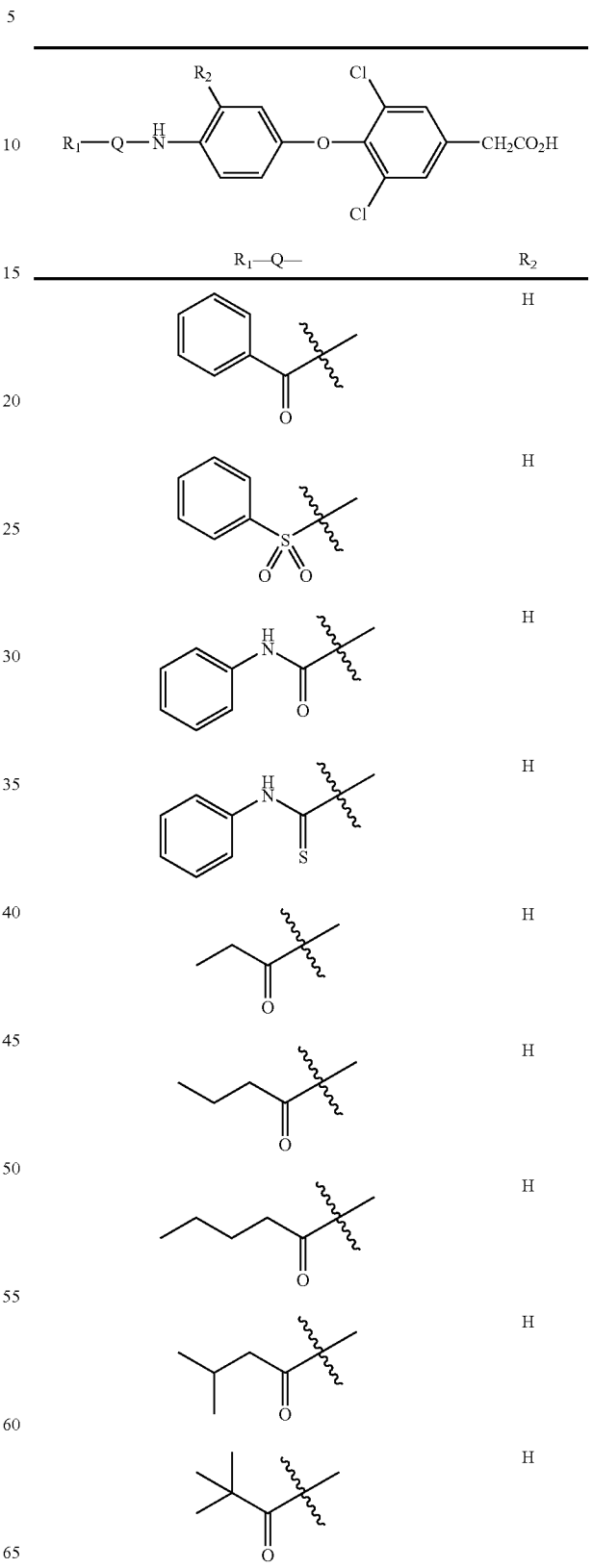

-continued
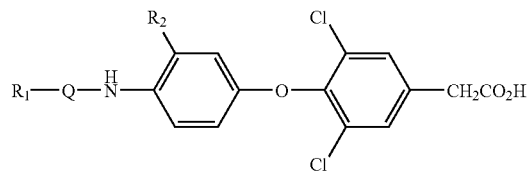
| $R_1$—Q— | $R_2$ |
|---|---|
| 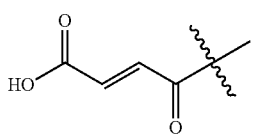 | H |
| 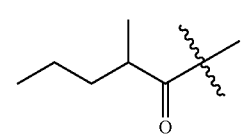 | H |
| 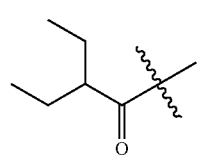 | H |
| 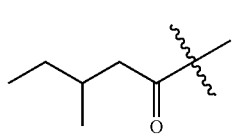 | H |
| 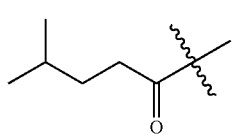 | H |
| 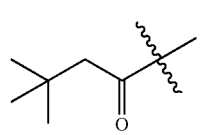 | H |
| 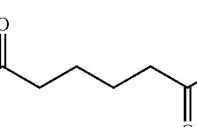 | H |
| 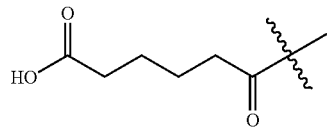 | H |
| 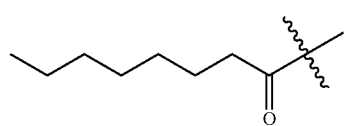 | H |
| 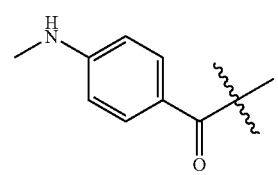 | H |
-continued
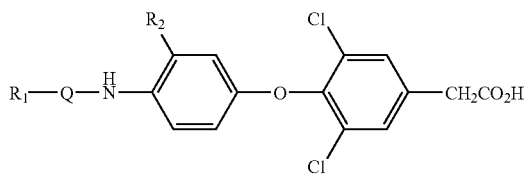
| $R_1$—Q— | $R_2$ |
|---|---|
| 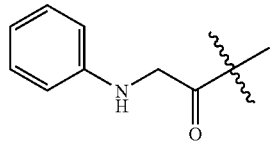 | H |
| 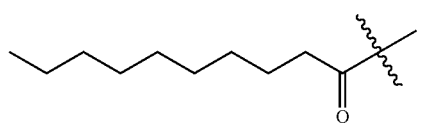 | H |
| 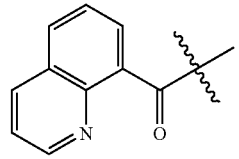 | H |
| 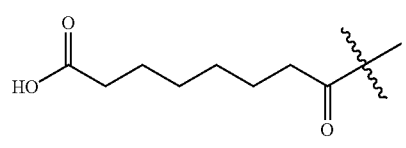 | H |
| 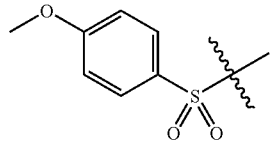 | H |
| 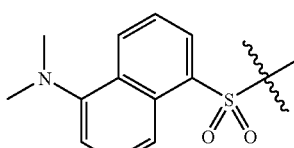 | H |
| 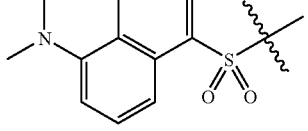 | Br |
| 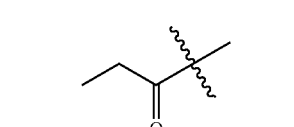 | Br |
| 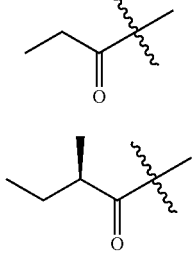 | Br |
| 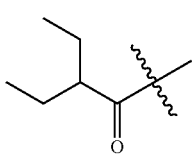 | |

-continued
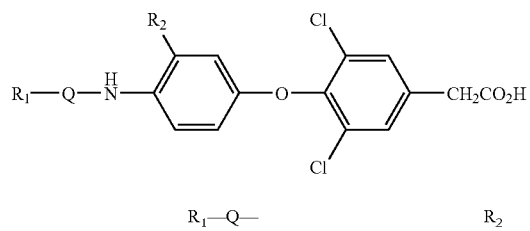
| $R_1-Q-$ | $R_2$ |
|---|---|
| 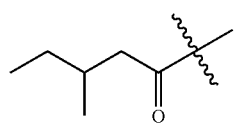 | Br |
| 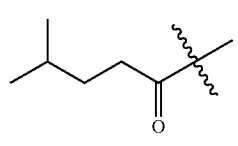 | Br |
| 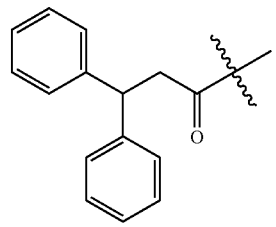 | Br |
| 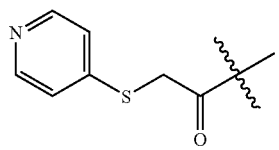 | Br |
| 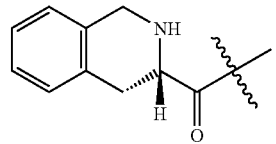 | H |
| 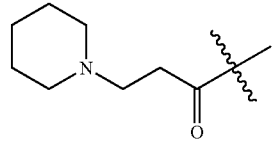 | B |
| 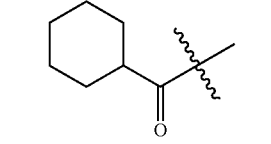 | H |
| 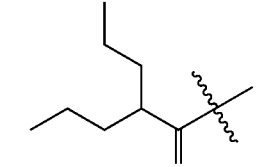 | H |
-continued
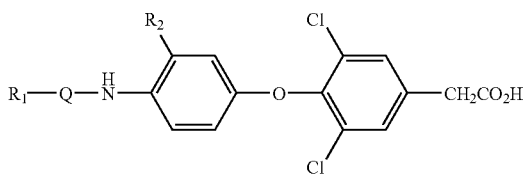
| $R_1-Q-$ | $R_2$ |
|---|---|
| 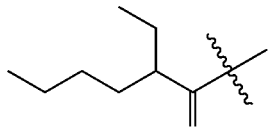 | H |
| 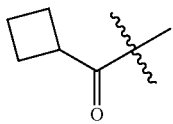 | H |
| 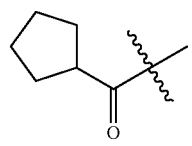 | H |
| 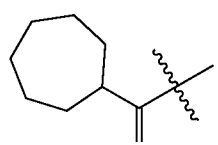 | H |
| 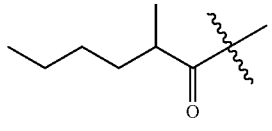 | H |
| 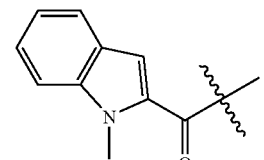 | H |
| 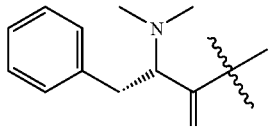 | H |
| 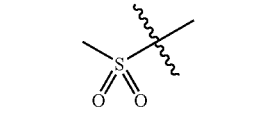 | H |
| 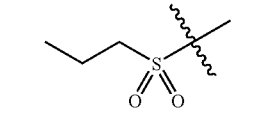 | H |
| 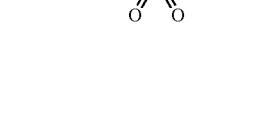 | H |

-continued
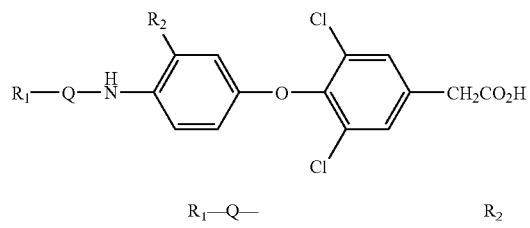
| R₁—Q— | R₂ |
|---|---|
| 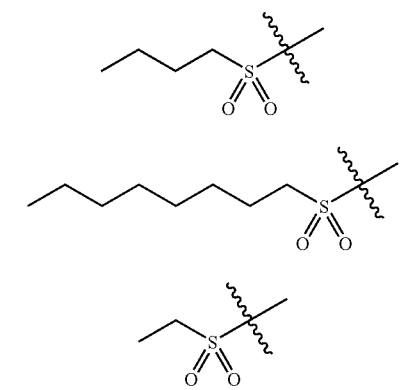 | H |
| | H |
| | H |
-continued
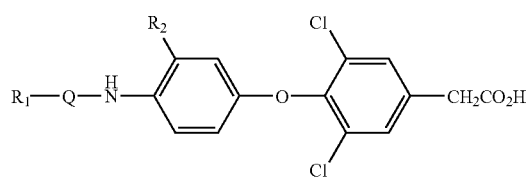
| R₁—Q— | R₂ |
|---|---|
| 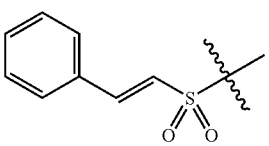 | H. |
* * * * *